(12) United States Patent
Kurita

(10) Patent No.: US 12,087,408 B2
(45) Date of Patent: Sep. 10, 2024

(54) CRYSTAL ANALYSIS METHOD, CRYSTAL ANALYSIS DEVICE, AND STORAGE MEDIUM

(71) Applicant: FUJITSU LIMITED, Kawasaki (JP)

(72) Inventor: Tomochika Kurita, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 386 days.

(21) Appl. No.: 17/502,087

(22) Filed: Oct. 15, 2021

(65) Prior Publication Data

US 2022/0199203 A1    Jun. 23, 2022

(30) Foreign Application Priority Data

Dec. 23, 2020 (JP) ................ 2020-213847

(51) Int. Cl.
 *G16C 20/20*    (2019.01)
(52) U.S. Cl.
 CPC ................. *G16C 20/20* (2019.02)
(58) Field of Classification Search
 None
 See application file for complete search history.

(56) References Cited

U.S. PATENT DOCUMENTS

2020/0381085 A1    12/2020    Jippo

FOREIGN PATENT DOCUMENTS

| JP | 2010-184899 A | 8/2010 |
|---|---|---|
| JP | 2012-025656 A | 2/2012 |
| WO | 2005/113441 A1 | 12/2005 |

OTHER PUBLICATIONS

Maritza Hernandez et al., "A Novel Graph-based Approach for Determining Molecular Similarity", arXiv:1601.06693v1 [cs.DS], pp. 1-16, Jan. 25, 2016, Internet URL:https://arxiv.org/pdf/1601.06693.pdf (Total 16 pages).

Momma, Koichi et al., "VESTA 3 for three-dimensional visualization of crystal, volumetric and morphology data", Journal of Applied Crystallography, vol. 44, No. 6, XP055812623, pp. 1272-1276, Oct. 29, 2011.

Extended European Search Report dated Apr. 25, 2022 for corresponding European Patent Application No. 21203113.2, 11 pages.

Chinese Office Action mailed Apr. 19, 2024 for Chinese Patent Application No. 202111292863.7, with English Translation, 23 pages.

*Primary Examiner* — Lisa M Caputo
*Assistant Examiner* — Cynthia L Davis
(74) *Attorney, Agent, or Firm* — Fujitsu Intellectual Property Center

(57) ABSTRACT

A crystal analysis method for a computer to execute a process includes creating a graph that indicates data of repeating unit cell in an ionic crystal and data of an adjacent repeating unit cell that is adjacent to the repeating unit cell; analyzing the ionic crystal based on the graph; and when a number of first intra-cell node that indicates data of an anionic atom bonded to a cationic atom in the repeating unit cell is n, setting a number of second intra-cell node that indicates data of the anionic atom in the repeating unit cell n−1 or less, wherein the data of repeating unit cell includes a plurality of intra-cell nodes that indicate data of atoms in the repeating unit cell, and the plurality of intra-cell nodes include the first intra-cell node and the second intra-cell node.

14 Claims, 36 Drawing Sheets

EXAMPLE OF RELATED ART

EMBODIMENT OF PRESENT APPLICATION

MOLECULE A:
ACETIC ACID

MOLECULE B:
METHYL ACETATE

MOLECULE A

MOLECULE B

SIZE: 3

FIG. 17

| COMBINATION OF NODES IN FIRST GRAPH AND SECOND GRAPH | A1 0 A2  B1 0 B2 | A1 1 A2  B1 0 B2 | A1 1 A2  B1 1 B2 | A1 1 A2  B1 2 B2 | A1 1 A2  B1 4 B2 | A1 2 A2  B1 3 B2 |
|---|---|---|---|---|---|---|
| $C_{ij}$ | 0 | 1 | 0 | $\frac{1}{2}$ | $\frac{3}{4}$ | $\frac{1}{3}$ |

| | | NUMBER OF BITS REQUIRED FOR CALCULATION | NUMBER OF ATOMS OF COMMON SUBSTRUCTURE | DEGREE OF SIMILARITY |
|---|---|---|---|---|
| EXAMPLE 1 | IONIC CRYSTAL A<br>NUMBER OF NODES 28 / IONIC CRYSTAL B<br>NUMBER OF NODES 40 | 416 | 18 | 0.546 |
| COMPARATIVE EXAMPLE 1 | NUMBER OF NODES 76 / NUMBER OF NODES 96 | 3104 | 55 | 0.648 |

FIG. 33

| NUMBER OF BITS REQUIRED FOR CALCULATION | NUMBER OF ATOMS OF COMMON SUBSTRUCTURE | DEGREE OF SIMILARITY |
|---|---|---|
| 2496 | 43 | 0.525 |

IONIC CRYSTAL B

NUMBER OF NODES
28×3=84

IONIC CRYSTAL A

EXAMPLE 2

NUMBER OF NODES
40×2=80

FIG. 34

EXAMPLE 3

| M | ICSD # | 174531 | 183602 | 195434 | 253224 | 107724 | 41433 |
|---|---|---|---|---|---|---|---|
| Fe | 174531 | 1.000 | 0.900 | 0.900 | 0.925 | 0.475 | 0.475 |
| Co | 183602 | 0.900 | 1.000 | 0.850 | 0.825 | 0.475 | 0.475 |
| Fe | 195434 | 0.900 | 0.850 | 1.000 | 0.825 | 0.475 | 0.475 |
| Mn | 253224 | 0.925 | 0.825 | 0.825 | 1.000 | 0.475 | 0.475 |
| Ba | 107724 | 0.475 | 0.475 | 0.475 | 0.475 | 1.000 | 0.950 |
| Ba | 41433 | 0.475 | 0.475 | 0.475 | 0.475 | 0.950 | 1.000 |

COMPARATIVE EXAMPLE 2

| M | ICSD # | 174531 | 183602 | 195434 | 253224 | 107724 | 41433 |
|---|---|---|---|---|---|---|---|
| Fe | 174531 | 1.000 | 0.958 | 0.958 | 0.958 | 0.788 | 0.771 |
| Co | 183602 | 0.958 | 1.000 | 0.917 | 0.917 | 0.788 | 0.771 |
| Fe | 195434 | 0.958 | 0.917 | 1.000 | 0.971 | 0.798 | 0.802 |
| Mn | 253224 | 0.958 | 0.917 | 0.917 | 1.000 | 0.788 | 0.771 |
| Ba | 107724 | 0.788 | 0.788 | 0.788 | 0.788 | 1.000 | 0.979 |
| Ba | 41433 | 0.771 | 0.771 | 0.771 | 0.771 | 0.979 | 1.000 |

FIG. 35

EXAMPLE 3

| M | ICSD# | 174531 | 183602 | 195434 | 253224 | 107724 | 41433 |
|---|---|---|---|---|---|---|---|
| Fe | 174531 | 832 | 832 | 832 | 832 | 736 | 832 |
| Co | 183602 | 832 | 832 | 832 | 832 | 736 | 832 |
| Fe | 195434 | 832 | 832 | 832 | 832 | 736 | 832 |
| Mn | 253224 | 832 | 832 | 832 | 832 | 736 | 0.475 |
| Ba | 107724 | 736 | 736 | 736 | 736 | 656 | 736 |
| Ba | 41433 | 832 | 832 | 832 | 832 | 736 | 832 |

COMPARATIVE EXAMPLE 2

| M | ICSD# | 174531 | 183602 | 195434 | 253224 | 107724 | 41433 |
|---|---|---|---|---|---|---|---|
| Fe | 174531 | 3968 | 3968 | 3968 | 3968 | 3872 | 3968 |
| Co | 183602 | 3968 | 3968 | 3968 | 3968 | 3872 | 3968 |
| Fe | 195434 | 3968 | 3968 | 3968 | 3968 | 3872 | 3968 |
| Mn | 253224 | 3968 | 3968 | 3968 | 3968 | 3872 | 3968 |
| Ba | 107724 | 3872 | 3872 | 3872 | 3872 | 3792 | 3872 |
| Ba | 41433 | 3968 | 3968 | 3968 | 3968 | 3872 | 3968 |

FIG. 36

| ICSD # | 257256 | 28938 | 28948 | 29128 | 44879 | 52235 |
|---|---|---|---|---|---|---|
| CsCl | 257256 | 1.000 | 0.375 | 0.375 | 0.375 | 0.375 | 0.375 |
| KCl | 28938 | 0.375 | 1.000 | 1.000 | 1.000 | 1.000 | 1.000 |
| NaCl | 28948 | 0.375 | 1.000 | 1.000 | 1.000 | 1.000 | 1.000 |
| NaF | 29128 | 0.375 | 1.000 | 1.000 | 1.000 | 1.000 | 1.000 |
| LiF | 44879 | 0.375 | 1.000 | 1.000 | 1.000 | 1.000 | 1.000 |
| LiCl | 52235 | 0.375 | 1.000 | 1.000 | 1.000 | 1.000 | 1.000 |

EXAMPLE 4

CRYSTAL ANALYSIS METHOD, CRYSTAL ANALYSIS DEVICE, AND STORAGE MEDIUM

CROSS-REFERENCE TO RELATED APPLICATION

This application is based upon and claims the benefit of priority of the prior Japanese Patent Application No. 2020-213847, filed on Dec. 23, 2020, the entire contents of which are incorporated herein by reference.

FIELD

The present application is related to a crystal analysis method, a crystal analysis device, and a storage medium.

BACKGROUND

In recent years, analysis on materials with use of a computer has been used for designing new materials, predicting characteristics of existing materials, searching for new uses of existing materials, and the like.

More specifically, for example, in computing a degree of similarity between molecules and a degree of similarity between crystals having a repeating structure, a "conflict graph" showing a combination of atoms in a structure for which the degree of similarity is computed can be used. As a technique of using the conflict graph, there has been proposed technology for specifying a degree of similarity by searching for a substructure common to each structure by solving a maximum independent set problem of a conflict graph with an annealing machine or the like.

Here, when determining a degree of similarity between crystals having a repeating structure, the number of atoms contained in each unit cell for the comparison of structures may increase (the number of bits required for computation of the degree of similarity may increase). In particular, for example, when the crystal is an ionic crystal, the unit cell contains a large number of anions (for example, oxygen atoms), and the number of atoms contained in the unit cell increases.

Furthermore, in a case of computing a degree of similarity with an annealing machine, it may be difficult to obtain an accurate degree of similarity when the number of atoms contained in the unit cell is large (the number of bits required for calculation is large) since the annealing machine has a limit on the number of bits that can be used in calculation.

Maritza Hernandez, Arman Zaribafiyan, Maliheh Aramon, Mohammad Naghibi "*A Novel Graph-based Approach for Determining Molecular Similarity*". arXiv: 1601.06693 (https://arxiv.org/pdf/1601.06693.pdf) is disclosed as related art.

SUMMARY

According to an aspect of the embodiments, a crystal analysis method for a computer to execute a process includes creating a graph that indicates data of repeating unit cell in an ionic crystal and data of an adjacent repeating unit cell that is adjacent to the repeating unit cell; analyzing the ionic crystal based on the graph; and when a number of first intra-cell node that indicates data of an anionic atom bonded to a cationic atom in the repeating unit cell is n, setting a number of second intra-cell node that indicates data of the anionic atom in the repeating unit cell n−1 or less, wherein the data of repeating unit cell includes a plurality of intra-cell nodes that indicate data of atoms in the repeating unit cell, and the plurality of intra-cell nodes include the first intra-cell node and the second intra-cell node.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 17 is a diagram illustrating an example of a relationship between a combination of nodes in a first graph and a second graph and $c'_{ij}$, which represents a weight regarding a bond order between cationic atoms;

FIG. 33 is a view illustrating a result of Example 2;

FIG. 34 is a view illustrating an example of a relationship between a type of an ionic crystal and a computed degree of similarity in Example 3 and Comparative Example 2;

FIG. 35 is a view illustrating an example of a relationship between a type of an ionic crystal and the number of bits required for calculating a degree of similarity in Example 3 and Comparative Example 2; and FIG. 36 is a view illustrating an example of a relationship between a type of an ionic crystal and a computed degree of similarity in Example 4.

DESCRIPTION OF EMBODIMENTS

An object of the present application is to provide a crystal analysis method, a crystal analysis device, and a crystal analysis program capable of reducing (suppressing) the number of bits required for analyzing an ionic crystal.

In one aspect, the present application can provide a crystal analysis method, a crystal analysis device, and a crystal analysis program capable of reducing (suppressing) the number of bits required for analyzing an ionic crystal.

(Crystal Analysis Method)

The technology disclosed in the present application is based on the finding of the present inventor that, in the related art, in analyzing an ionic crystal, the number of bits required for calculation increases when the number of atoms contained in a unit cell of the ionic crystal is large, and accurate analysis may be difficult. Therefore, before describing details of the technology disclosed in the present application, problems and the like of the related art will be described.

As described above, in performing an analysis of computing a degree of similarity between molecules and a degree of similarity between crystals having a repeating structure, for example, it is possible to use technology using a "conflict graph" showing a combination of atoms in a structure for which the degree of similarity is computed. In this technology, for example, a degree of similarity can be obtained by searching for a maximum independent set (solving a maximum independent set problem) for a conflict graph, to specify a substructure common to each structure.

Here, in computing the degree of similarity in structure between compounds by solving the maximum independent set problem in the conflict graph, the compounds are expressed as graphs to be handled. Here, to express a compound as a graph means to represent the structure of the compound by using, for example, information on a type of atoms (elements) in the compound and information on a bonding state between the individual atoms.

In the following, a method for creating the conflict graph will be described by taking, as an example, a case of creating a conflict graph of acetic acid ($CH_3COOH$) and methyl acetate ($CH_3COOCH_3$) first, as an example of obtaining a degree of similarity between molecules.

Figure 1:
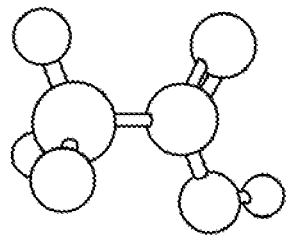
FIG. 1 is a diagram illustrating an example of a state of expressing acetic acid and methyl acetate as graphs.
Figure 1:
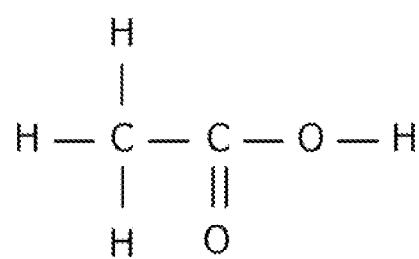
Figure 1:
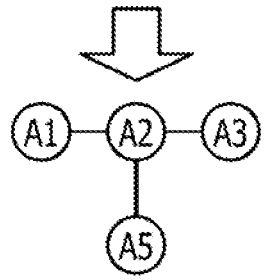
Figure 1:
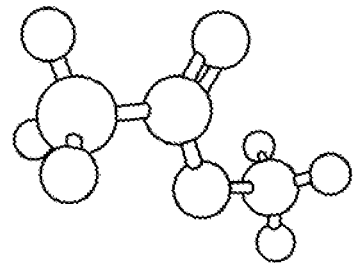
Figure 1:
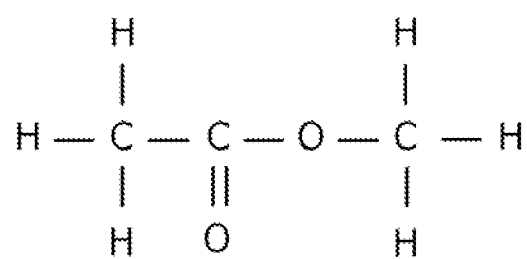
Figure 1:
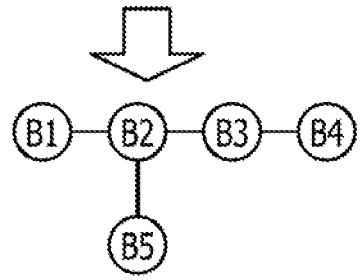

First, acetic acid (hereinafter sometimes referred to as "molecule A") and methyl acetate (hereinafter sometimes referred to as "molecule B") are expressed as graphs, and are given as illustrated in FIG. 1. In FIG. 1, atoms that form acetic acid are indicated by A1, A2, A3, and A5, and atoms that form methyl acetate are indicated by B1 to B5. Furthermore, in FIG. 1, A1, A2, B1, B2, and B4 indicate carbon, and A3, A5, B3, and B5 indicate oxygen, while a single bond is indicated by a thin solid line and a double bond is indicated by a thick solid line.

Figure 2:
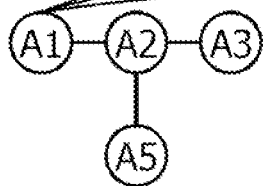
FIG. 2 is a diagram illustrating an example of combinations in a case of combining the same elements in molecules A and B and making nodes of a conflict graph.
Figure 2:
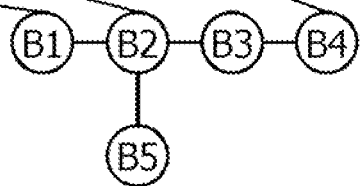
Figure 2:
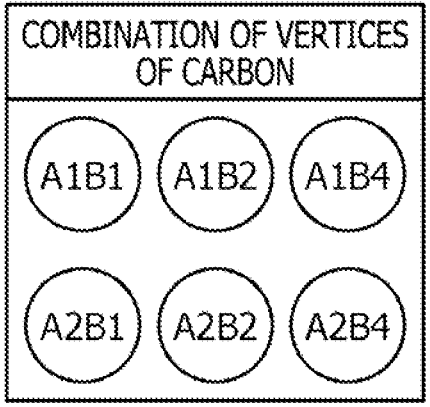
Figure 2:
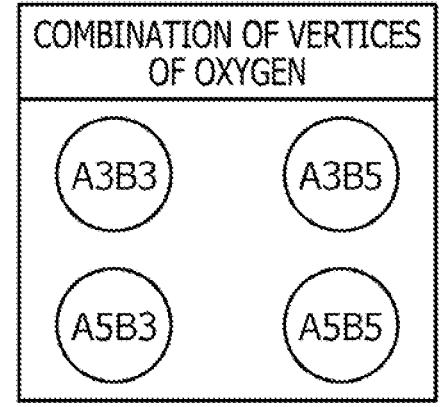

Next, vertices (atoms) in the molecules A and B expressed as a graph are combined to create vertices (nodes) of a conflict graph. At this time, for example, as illustrated in FIG. 2, it is favorable to combine the same elements in the molecules A and B to create nodes of the conflict graph. In the example illustrated in FIG. 2, combinations of A1, A2, B1, B2, and B4 that represent carbon and combinations of A3, A5, B3, and B5 that represent oxygen are employed as nodes of the conflict graph.

Subsequently, edges (branches or sides) in the conflict graph are created. At this time, two nodes are compared, and when the nodes are constituted by atoms in different situations from each other (for example, an atomic number, the presence or absence of a bond, a bond order, or the like), an edge is created between these two nodes. Whereas, when two nodes are compared and the nodes are constituted by atoms in the same situation, no edge is created between these two nodes.

Here, a rule for creating the edge in the conflict graph will be described with reference to FIG. 3.

First, in the example illustrated in FIG. 3, whether or not an edge is created between a node [A1B1] and a node [A2B2] will be described. As can be seen from the structure of the molecule A expressed as a graph in FIG. 3, the carbon A1 of the molecule A included in the node [A1B1] and the carbon A2 of the molecule A included in the node [A2B2] are bonded (single bonded) to each other. Likewise, the carbon B1 of the molecule B included in the node [A1B1] and the carbon B2 of the molecule B included in the node [A2B2] are bonded (single bonded) to each other. In other words, for example, the situation of bonding between the carbons A1 and A2 and the situation of bonding between the carbons B1 and B2 are identical to each other.

Figure 3:
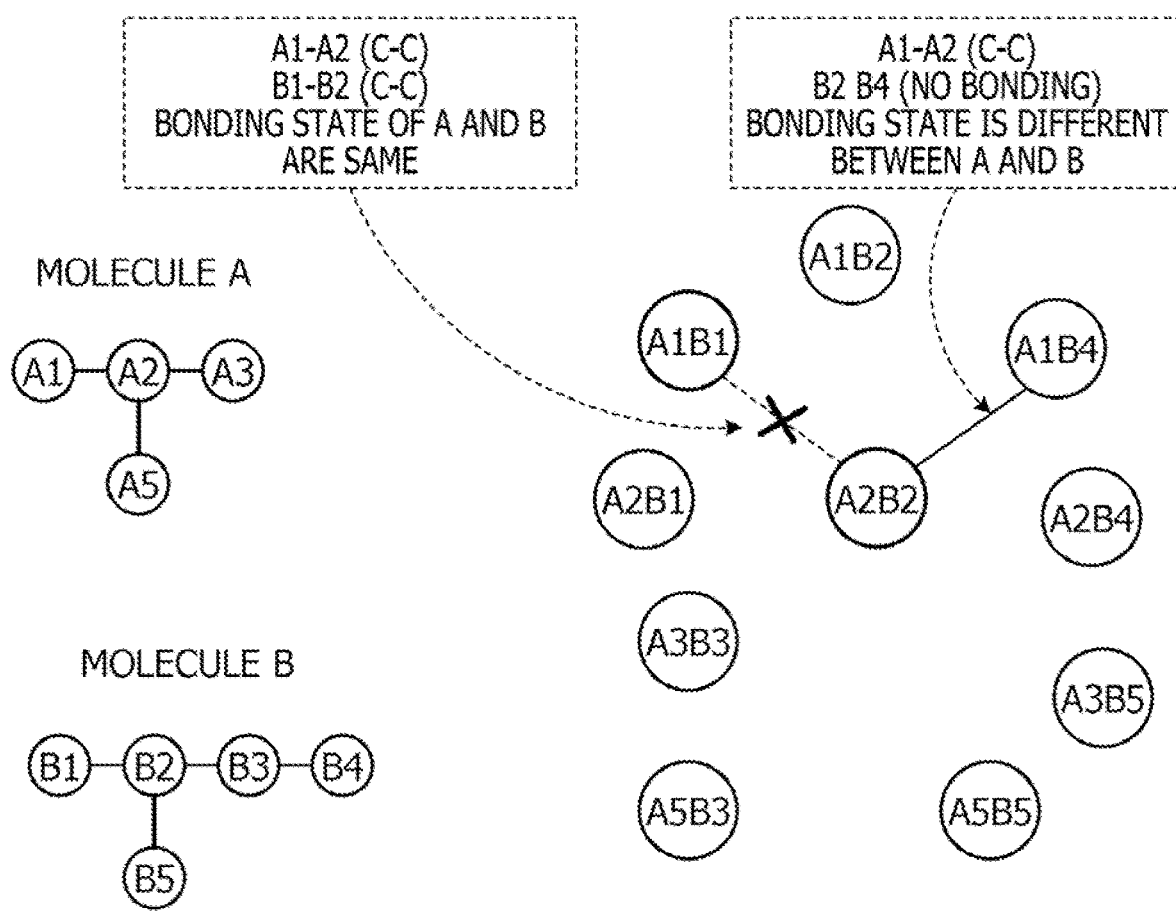
FIG. 3 is a diagram illustrating an example of a rule for creating an edge in the conflict graph.

In this manner, in the example in FIG. 3, the situation of the carbons A1 and A2 in the molecule A and the situation of the carbons B1 and B2 in the molecule B are identical to each other, and the nodes [A1B1] and [A2B2] are deemed as nodes constituted by atoms in identical situations to each other. Therefore, in the example illustrated in FIG. 3, no edge is created between the nodes [A1B1] and [A2B2].

Next, in the example illustrated in FIG. 3, whether or not an edge is created between a node [A1B4] and the node [A2B2] will be described. As can be seen from the structure of the molecule A expressed as a graph in FIG. 3, the carbon A1 of the molecule A included in the node [A1B4] and the carbon A2 of the molecule A included in the node [A2B2] are bonded (single bonded) to each other. Whereas, as can be seen from the structure of the molecule B expressed as a graph, the carbon B4 of the molecule B included in the node [A1B4] and the carbon B2 of the molecule B included in the node [A2B2] have the oxygen B3 sandwiched between the carbons B4 and B2, and are not directly bonded. In other words, for example, the situation of bonding between the carbons A1 and A2 and the situation of bonding between the carbons B4 and B2 are different from each other.

That is, for example, in the example in FIG. 3, the situation of the carbons A1 and A2 in the molecule A and the situation of the carbons B4 and B2 in the molecule B are different from each other, and the nodes [A1B4] and [A2B2] are deemed as nodes constituted by atoms in different situations from each other. Therefore, in the example illustrated in FIG. 3, an edge is created between the nodes [A1B4] and [A2B2].

In this manner, the conflict graph can be created based on the rule that, when nodes are constituted by atoms in different situations, an edge is created between these nodes, and when nodes are constituted by atoms in the same situation, no edge is created between these nodes.

Figure 4:
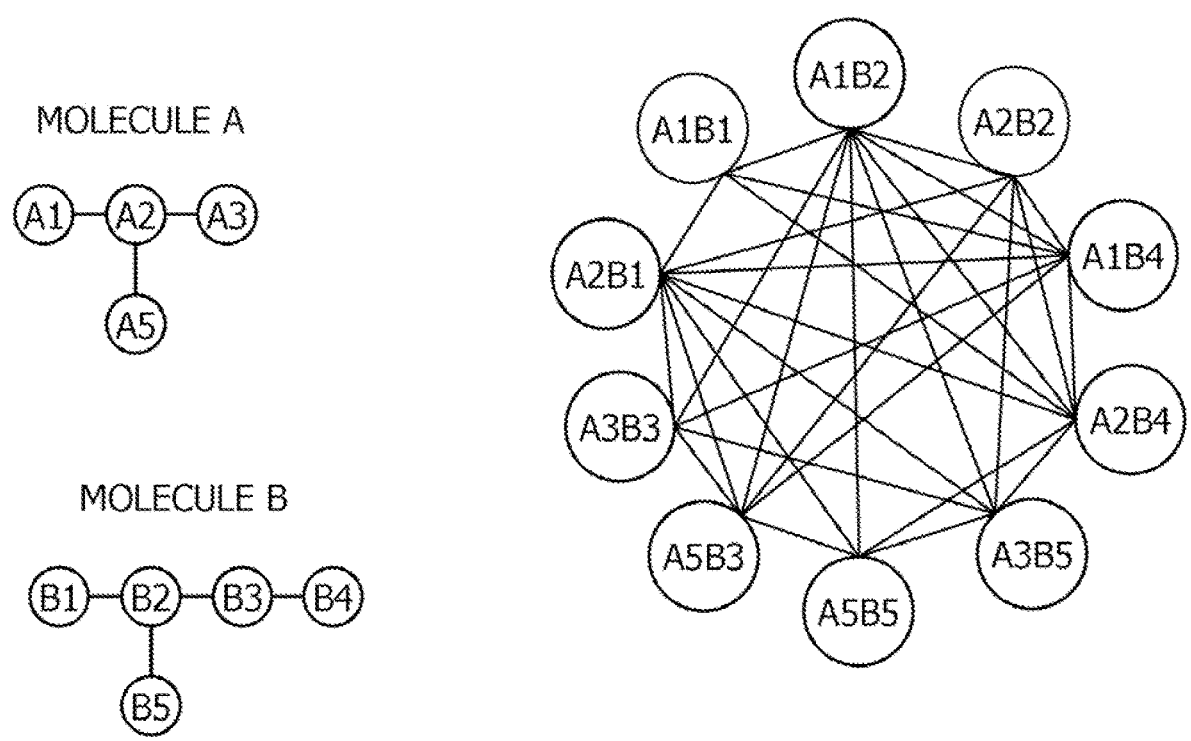
FIG. 4 is a diagram illustrating an example of the conflict graph of the molecules A and B.

FIG. 4 is a diagram illustrating an example of a conflict graph of the molecules A and B. As illustrated in FIG. 4, for example, in the node [A2B2] and a node [A5B5], the situation of bonding between the carbon A2 and the oxygen A5 in the molecule A and the situation of bonding between the carbons B2 and B5 in the molecule B are identical to each other. Therefore, the nodes [A2B2] and [A5B5] are deemed as nodes constituted by atoms in identical situations to each other, and thus no edge has been created between the nodes [A2B2] and [A5B5].

Next, an example of a method for solving the maximum independent set problem of the created conflict graph will be described.

The maximum independent set (MIS) in the conflict graph means a set that includes the largest number of nodes that do not have edges between the nodes among sets of nodes constituting the conflict graph. In other words, for example, the maximum independent set in the conflict graph means a set that has the maximum size (number of nodes) among sets formed by nodes that have no edges between the nodes with each other.

Figure 5:
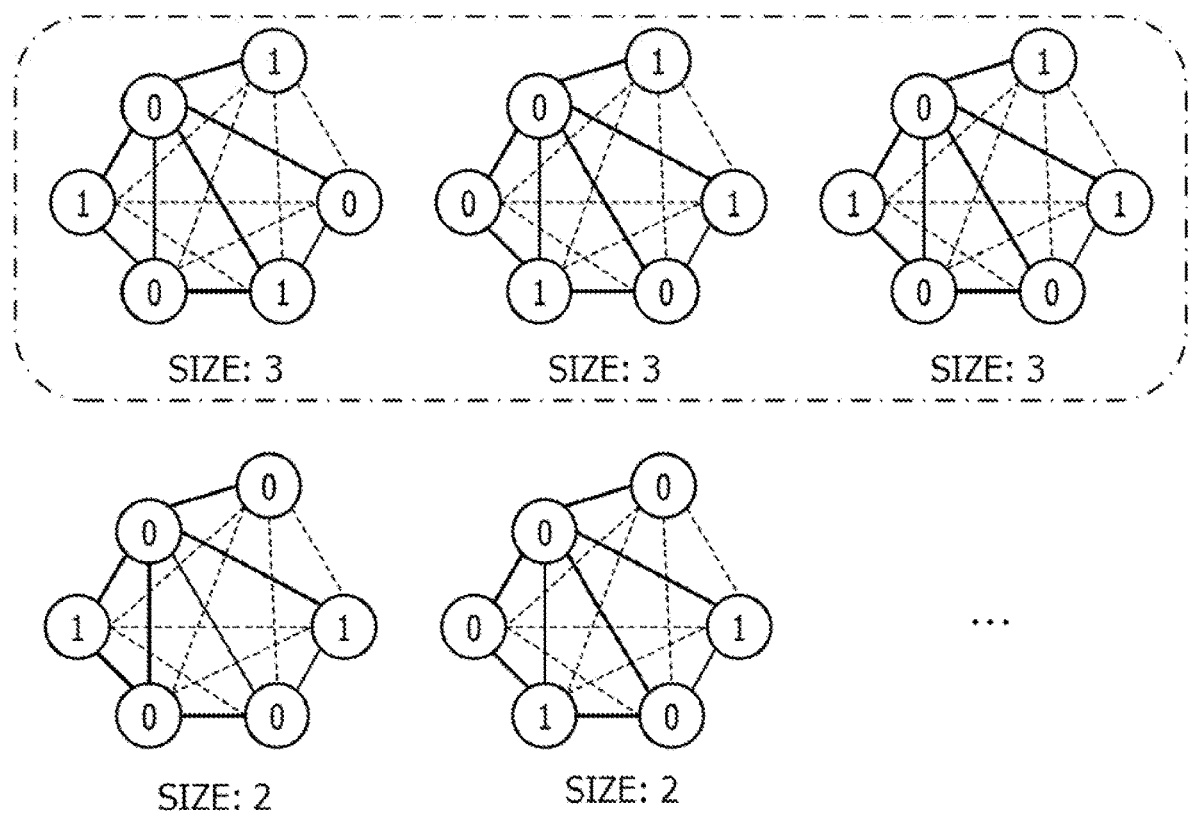
FIG. 5 is a diagram illustrating an example of a maximum independent set in the graph.

FIG. 5 is a diagram illustrating an example of a maximum independent set in a graph. In FIG. 5, nodes included in a set are marked with a reference sign of "1", and nodes not included in any set are marked with a reference sign of "0"; for instances where edges are present between nodes, the nodes are connected by solid lines, and for instances where no edges are present, the nodes are connected by dotted lines. Note that, here, as illustrated in FIG. 5, a graph of which the number of nodes is six will be described as an example for simplification of explanation.

In the example illustrated in FIG. 5, among sets constituted by nodes that have no edges between the nodes, there are three sets having the maximum number of nodes, and the number of nodes in each of these sets is three. In other words, for example, in the example illustrated in FIG. 5, three sets surrounded by a one-dot chain line are given as the maximum independent sets in the graph.

Here, as described above, the conflict graph is created based on the rule that, when nodes are constituted by atoms in different situations, an edge is created between these nodes, and when nodes are constituted by atoms in the same situation, no edge is created between these nodes. Therefore, in the conflict graph, working out the maximum independent set, which is a set having the maximum number of nodes among sets constituted by nodes that have no edges between the nodes, is synonymous with working out the largest substructure among substructures common to two molecules. In other words, for example, the largest common substructure of two molecules can be specified by working out the maximum independent set in the conflict graph.

Figure 6:
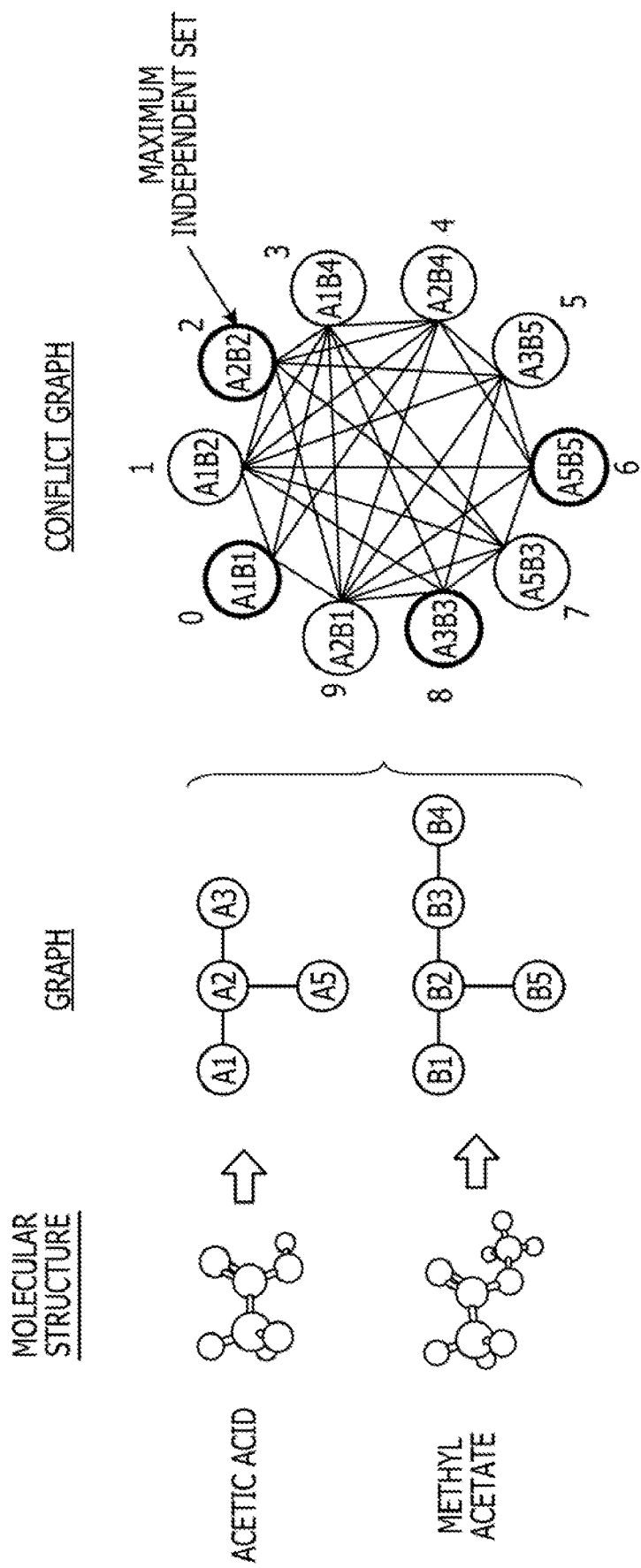
FIG. 6 is a diagram illustrating an example of a flow in a case of finding a maximum common substructure between the molecule A and the molecule B by finding a maximum independent set of the conflict graph (by solving a maximum independent set problem)

FIG. 6 illustrates an example of a flow in a case where a maximum common substructure of the molecule A (acetic acid) and the molecule B (methyl acetate) is worked out (a maximum independent set problem is solved) by working out the maximum independent set in the conflict graph. As illustrated in FIG. 6, a conflict graph is created in such a manner that the molecules A and B are each expressed as a graph, the same elements are combined and employed as a node, and an edge is formed according to the situation of atoms constituting the node. Then, by working out the maximum independent set in the created conflict graph, the maximum common substructure of the molecules A and B can be worked out.

Here, an example of a specific method for working out (searching for) the maximum independent set in the conflict graph will be described.

A maximum independent set in the conflict graph may be searched for by, for example, using a Hamiltonian in which minimizing means searching for the maximum independent set. More specifically, for example, the search can be performed by using a Hamiltonian (H) indicated by the following equation.

[Formula 1]
$$H = -\alpha \sum_{i=0}^{n-1} b_i x_i + \beta \sum_{i,j=0}^{n-1} w_{ij} x_i x_j$$

Here, in the above equation, n denotes the number of nodes in the conflict graph, and $b_i$ denotes a numerical value that represents a bias for an i-th node.

Moreover, $w_{ij}$ has a positive non-zero number when there is an edge between the i-th node and a j-th node, and has zero when there is no edge between the i-th node and the j-th node.

Furthermore, $x_i$ represents a binary variable representing that the i-th node has 0 or 1, and $x_j$ represents a binary variable representing that the j-th node has 0 or 1.

Note that $\alpha$ and $\beta$ are positive numbers.

A relationship between the Hamiltonian represented by the above equation and the search for the maximum independent set will be described in more detail. The above equation is a Hamiltonian that represents an Ising model equation in the quadratic unconstrained binary optimization (QUBO) format.

In the above equation, when $x_i$ has 1, it means that the i-th node is included in a set that is a candidate for the maximum independent set, and when $x_i$ has 0, it means that the i-th node is not included in a set that is a candidate for the maximum independent set. Likewise, in the above equation, when $x_j$ has 1, it means that the j-th node is included in a set that is a candidate for the maximum independent set, and when $x_j$ has 0, it means that the j-th node is not included in a set that is a candidate for the maximum independent set.

Therefore, in the above equation, by searching for a combination in which as many nodes as possible have the state of 1 under the constraint that there is no edge between nodes whose states are designated as 1 (bits are designated as 1), the maximum independent set can be searched.

Here, each term in the above equation will be described.

The first term on the right side of the above equation (the term with a coefficient of $-\alpha$) is a term whose value becomes smaller as the number of i whose $x_i$ has 1 is larger (the number of nodes included in a set that is a candidate for the maximum independent set is larger). Note that the value of the first term on the right side of the above equation becoming smaller means that a larger negative number is given. That is, for example, in the above equation, the value of the Hamiltonian (H) becomes smaller when many nodes have the bit of 1, due to an action of the first term on the right side.

The second term on the right side of the above equation (the term with a coefficient of $\beta$) is a term of a penalty whose value becomes larger when there is an edge between nodes whose bits have 1 (when has a positive non-zero number). In other words, for example, the second term on the right side of the above equation has 0 when there is no instance where an edge is present between nodes whose bits have 1, and has a positive number in other cases. That is, for example, in the above equation, the value of the Hamiltonian (H) becomes larger when there is an edge between nodes whose bits have 1, due to an action of the second term on the right side.

As described above, the above equation has a smaller value when many nodes have the bit of 1, and has a larger value when there is an edge between the nodes whose bits have 1; accordingly, it can be said that minimizing the above equation means searching for the maximum independent set.

Here, the relationship between the Hamiltonian represented by the above equation and the search for the maximum independent set will be described using an example with reference to the drawings.

Figure 7:
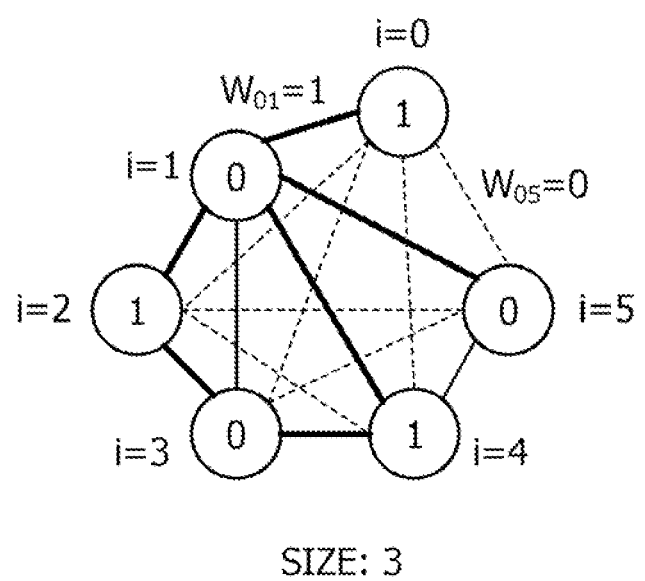
FIG. 7 is an explanatory diagram for describing an example of a technique of searching for a maximum independent set in a graph of which the number of nodes is six.

A case where the bit is set in each node as in the example illustrated in FIG. 7 in a graph of which the number nodes is six will be considered. In the example in FIG. 7, similarly to FIG. 5, for instances where edges are present between nodes, the nodes are connected by solid lines, and for instances where no edges are present, the nodes are connected by dotted lines.

For the example in FIG. 7, assuming in the above equation that $b_i$ has 1, and $w_{ij}$ has 1 when there is an edge between the i-th node and the j-th node, the above equation is as follows.

[Formula 2]
$$H = -\alpha(x_0 + x_1 + x_2 + x_3 + x_4 + x_5) +$$
$$\beta(\lambda_{01} x_0 x_1 + \lambda_{02} x_0 x_2 + \lambda_{03} x_0 x_3 + \lambda_{04} x_0 x_4 + \lambda_{05} x_0 x_5 + \dots) =$$
$$-\alpha(1 + 0 + 1 + 0 + 1 + 0) +$$
$$\beta(1*1*0 + 0*1*1 + 0*1*0 + 0*1*1 + 0*1*0 + \dots) = -3\alpha$$

In this manner, in the example in FIG. 7, when there is no instance where an edge is present between nodes whose bits have 1 (when there is no contradiction as an independent set), the second term on the right side has 0, and the value of the first term is given as the value of the Hamiltonian as it is.

Figure 8:
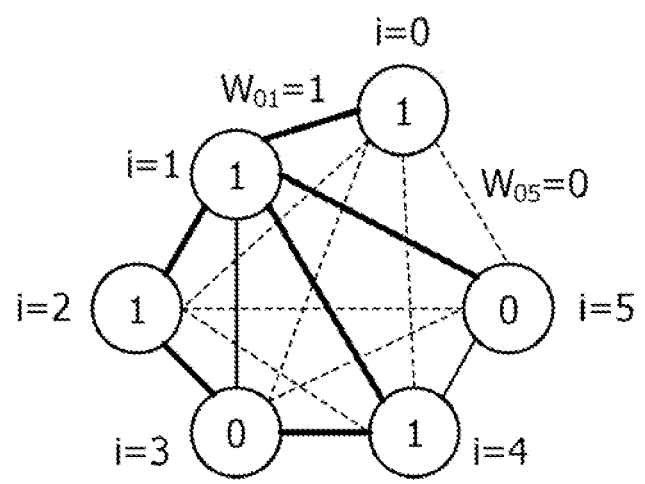
FIG. 8 is an explanatory diagram for describing an example of a technique of searching for a maximum independent set in a graph of which the number of nodes is six.

Next, a case where the bit is set in each node as in the example illustrated in FIG. 8 will be considered. Similarly to the example in FIG. 7, assuming in the above equation that $b_i$ has 1, and $w_{ij}$ has 1 when there is an edge between the i-th node and the j-th node, the above equation is as follows.

[Formula 3]
$$H = -\alpha(x_0 + x_1 + x_2 + x_3 + x_4 + x_5) +$$
$$\beta(\lambda_{01} x_0 x_1 + \lambda_{02} x_0 x_2 + \lambda_{03} x_0 x_3 + \lambda_{04} x_0 x_4 + \lambda_{05} x_0 x_5 + \dots)$$
$$= -\alpha(1 + \underline{1} + 1 + 0 + 1 + 0) +$$
$$\beta(1*1*\underline{1} + 0*1*1 + 0*1*0 + 0*1*1 + 0*1*0 + \dots)$$
$$= -4\alpha + 5\beta$$

In this manner, in the example in FIG. 8, since there is an instance where an edge is present between nodes whose bits have 1, the second term on the right side does not have 0, and the value of the Hamiltonian is given as the sum of the two terms on the right side. Here, in the examples illustrated in FIGS. 7 and 8, for example, when $\alpha > 5\beta$ is assumed, $-3\alpha < -4\alpha + 5\beta$ is satisfied, and accordingly, the value of the Hamiltonian in the example in FIG. 7 is smaller than the value of the Hamiltonian in the example in FIG. 8. In the example in FIG. 7, a set of nodes that has no contradiction as the maximum independent set is obtained, and it can be seen that the maximum independent set can be retrieved by searching for a combination of nodes in which the value of the Hamiltonian in the above Equation (1) becomes smaller.

Next, an example of a method for computing a degree of similarity in structure between molecules on the basis of the searched maximum independent set will be described.

The degree of similarity in structure between molecules can be computed, for example, using the following equation.

[Formula 4]
$$S(G_A, G_B) = \delta\max\left\{\frac{|V_C^A|}{|V_A|}, \frac{|V_C^B|}{|V_B|}\right\} + (1-\delta)\min\left\{\frac{|V_C^A|}{|V_A|}, \frac{|V_C^B|}{|V_B|}\right\}$$

Here, in the above equation of the degree of similarity, $S(G_A, G_B)$ represents a degree of similarity between a first molecule expressed as a graph (for example, a molecule A) and a second molecule expressed as a graph (for example, a molecule B), is represented as 0 to 1, and means that the closer to 1, the higher the degree of similarity.

Furthermore, $V_A$ represents a total number of node atoms of the first molecule expressed as a graph, and $V_C^A$ represents the number of node atoms included in the maximum independent set of the conflict graph among node atoms of the first molecule expressed as a graph. Note that the node atom means an atom at a vertex of the molecule expressed as a graph.

Moreover, $V_B$ represents a total number of node atoms of the second molecule expressed as a graph, and $V_C^B$ represents the number of node atoms included in the maximum independent set of the conflict graph among node atoms of the second molecule expressed as a graph.

$\delta$ denotes a number from 0 to 1.

Furthermore, in the above equation of the degree of similarity, max {A, B} means to select a larger value from among A and B, and min {A, B} means to select a smaller value from among A and B.

Here, similarly to the examples illustrated in FIGS. 1 to 8, a method for computing a degree of similarity will be described taking acetic acid (molecule A) and methyl acetate (molecule B) as examples.

Figure 9:
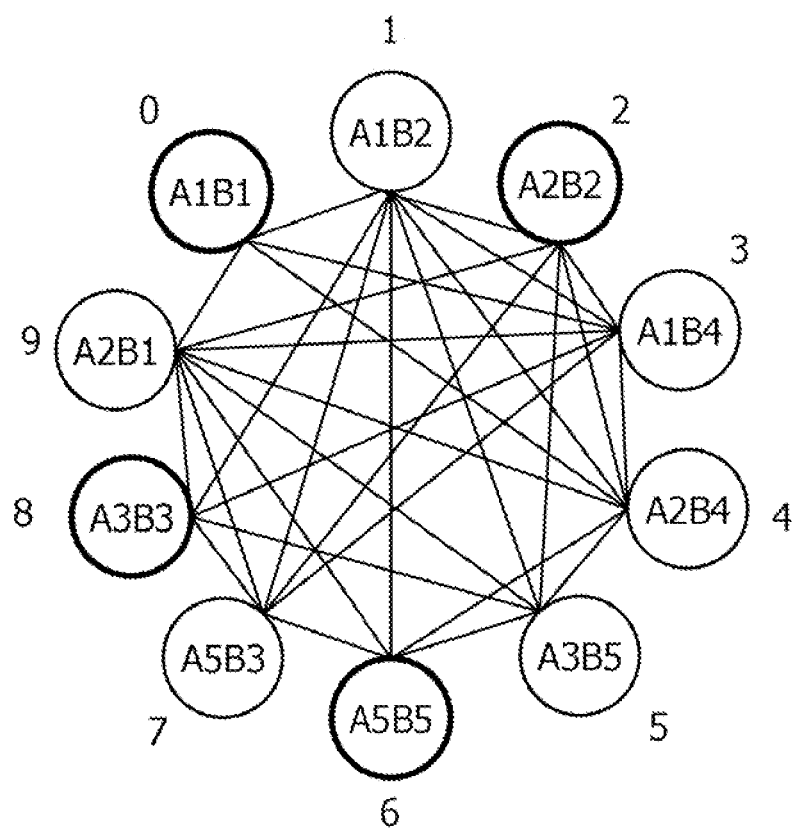
FIG. 9 is a diagram illustrating an example of a maximum independent set in a conflict graph.

In a conflict graph illustrated in FIG. 9, the maximum independent set is constituted by four nodes: a node [A1B1], a node [A2B2], a node [A3B3], and a node [A5B5]. That is, for example, in the example in FIG. 9, $|V_A|$ is given as 4, $|V_C^A|$ is given as 4, $|V_B|$ is given as 5, and $|V_C^B|$ is given as 4. Furthermore, in this example, when it is assumed that $\delta$ has 0.5 and an average of the first molecule and the second molecule is taken (treated equally), the above equation of the degree of similarity is as follows.

[Formula 5]
$$S(G_A, G_B) = 0.5 * \max\left\{\frac{4}{4}, \frac{4}{5}\right\} + (1-0.5)*\min\left\{\frac{4}{4}, \frac{4}{5}\right\}$$
$$= 0.5 * \frac{4}{4} + (1-0.5)*\frac{4}{5} = 0.9$$

In this manner, in the example in FIG. 9, the degree of similarity in structure between molecules can be computed as 0.9 on the basis of the above equation of the degree of similarity.

Although the technique for calculating the degree of similarity between molecules has been described in detail above, a similar technique can also be appropriately used also in a case of calculating the degree of similarity between crystals having a repeating structure.

Here, in a case of calculating the degree of similarity between crystals, since the crystal has a repeating structure (periodic structure, crystalline structure) in which a unit cell is three-dimensionally repeated, it is required to properly express this repeating structure in order to calculate the degree of similarity with high accuracy.

Figure 10:
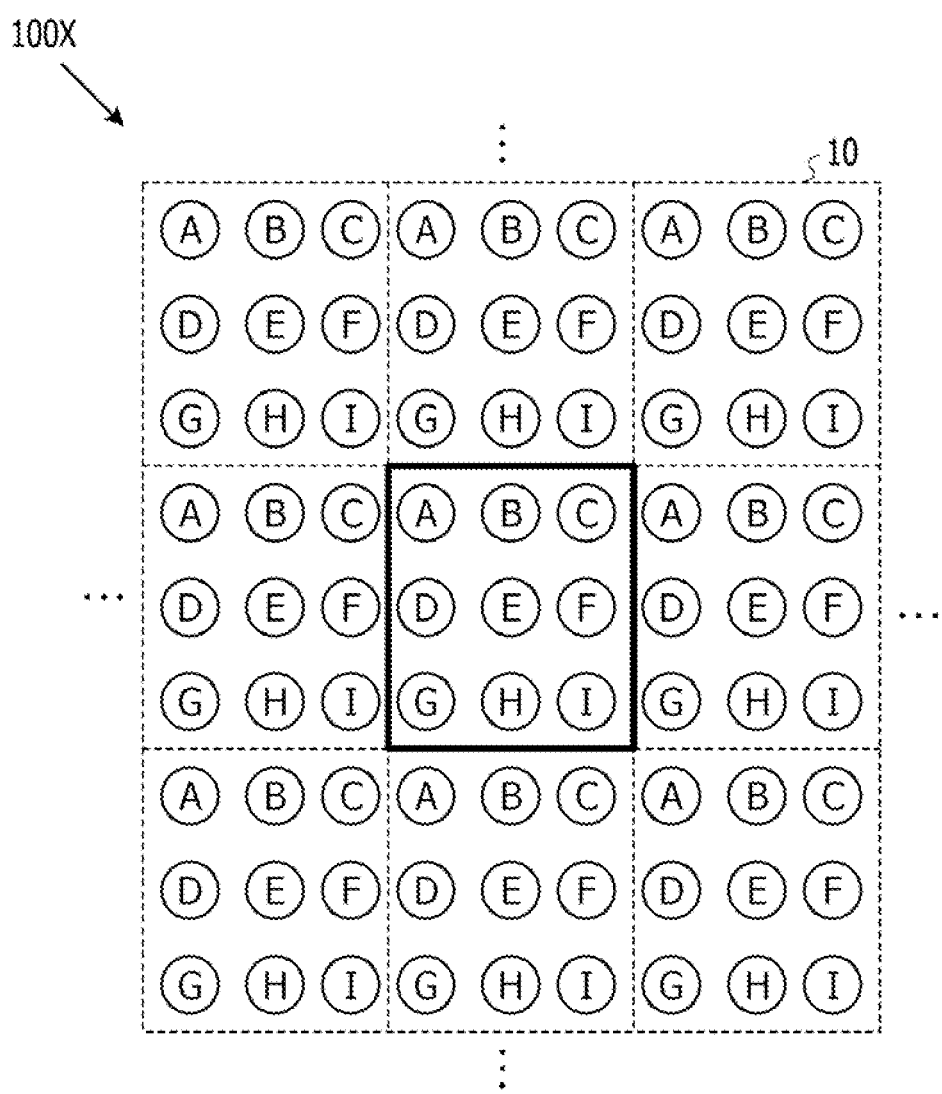
FIG. 10 is a schematic diagram illustrating an example of a periodic structure in a crystal (crystalline material) having a repeating structure.

FIG. 10 illustrates a schematic diagram of an example of a periodic structure of a crystal (crystalline material) having a repeating structure. In the example illustrated in FIG. 10, a crystal 10X has a structure in which a unit cell 10 containing nine distinguishable types of atoms (atoms A to I) is repeated. Note that FIG. 10 illustrates a structure in which atoms and unit cells are arranged two-dimensionally for convenience of explanation, but an actual crystal has a structure in which atoms and unit cells are arranged three-dimensionally. Furthermore, in FIG. 10, dotted lines at the top, bottom, left, and right mean that the unit cell 10 is repeated.

As illustrated in FIG. 10, the crystal 10X is a set of a large number of unit cells 10. Therefore, in analyzing the crystal 10X (calculation of a degree of similarity, and the like), it is required to consider not only the atoms included in one unit cell 10 but also the atoms included in the unit cell 10 existing therearound.

As an example of a technique for obtaining a degree of similarity of crystals in consideration of the repeating structure in the crystal, there is exemplified a technique of extending and handling one unit cell so as to include atoms (extension nodes) of other unit cells adjacent to the one unit cell, regarding the repeating unit cell in the crystal.

Figure 11:
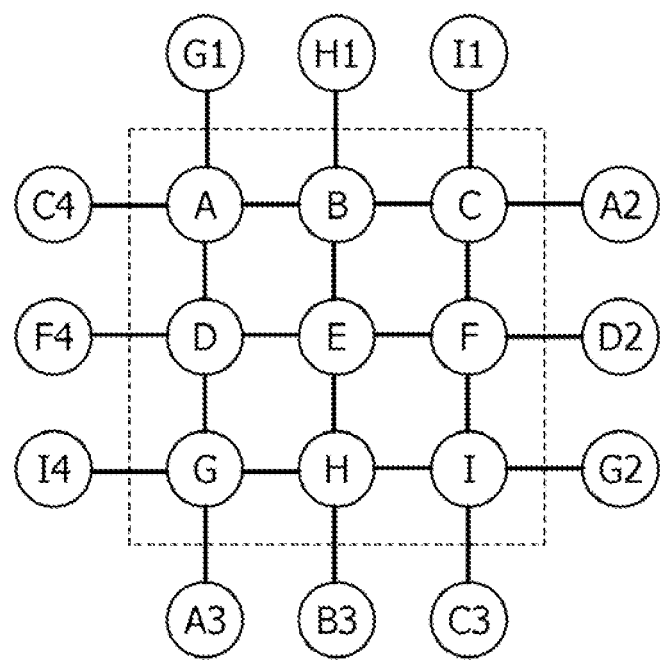
FIG. 11 is a diagram illustrating an example of a unit cell in a technique of extending and handling a unit cell by using an extension node.

This technique will be described with reference to FIG. 11. As illustrated in FIG. 11, in the technique of extending and handling the unit cell by using the extension nodes, for example, the nodes representing the atoms A to I are designated as nodes A to I, respectively. Then, in this technique, for example, individual nodes of atoms (nodes in the cell) are connected by an edge so as to correspond to a chemical bond between the atoms in the crystal.

Moreover, in the technique of extending the unit cell by using the extension nodes, for example, in another unit cell adjacent to one unit cell containing the atoms A to I, a node corresponding to an atom adjacent to and bonded to the atom of the one unit cell is prepared as an extension node. In the example illustrated in FIG. 11, for example, for a node A, there are prepared an extension node G1 corresponding to an atom G in a unit cell adjacent to an upper side of the unit cell containing the node A, and an extension node C4 corresponding to an atom C in a unit cell adjacent to a left side of the unit cell containing the node A. Similarly, as illustrated in FIG. 11, for the nodes A to I, extension nodes corresponding to atoms in adjacent unit cells are prepared.

Next, as illustrated in FIG. 11, for the nodes A to I, edges (extension edges) between with the prepared extension nodes are created so as to correspond to the chemical bonds between the atoms in the crystal.

In this way, in the technique of extending and handling the unit cell by using the extension nodes, by using, for one unit cell, an extension node corresponding to an atom in another unit cell adjacent to the one unit cell, the one unit cell is extended in consideration of a bonding state of atoms in the crystal. By doing this, in the technique of extending and handling the unit cell by using the extension nodes, since the repeating structure of the unit cell in the crystal can be appropriately expressed, the analysis (computation of a degree of similarity, and the like) targeted at the crystal can be performed with high accuracy.

Furthermore, as another example of the technique that considers the repeating structure of the crystal, there is exemplified a technique of, regarding the unit cell in the crystal, specifying atoms in one unit cell corresponding to atoms in another unit cell adjacent to the one unit cell, and expressing as a loop structure.

Figure 12:
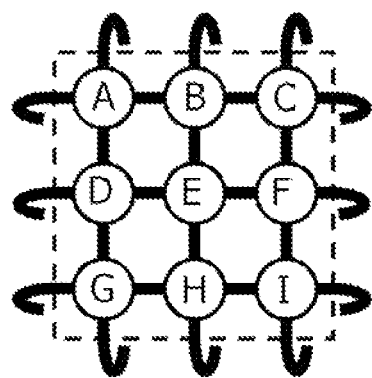
FIG. 12 is a diagram illustrating an example of a unit cell in a technique of treating a repeating structure of a crystal as a loop structure.

This technique will be described with reference to FIG. 12. As illustrated in FIG. 12, in the technique of treating the repeating structure of the crystal as a loop structure, for example, similarly to the example of FIG. 11, the nodes representing atoms A to I are designated as the nodes A to I, respectively. Then, in this technique, similarly to the example of FIG. 11, individual nodes of atoms (nodes in the cell) are connected by an edge so as to correspond to a chemical bond between the atoms in the crystal.

Moreover, as illustrated in FIG. 12, in the technique of treating the repeating structure of the crystal as a loop structure, for example, a loop edge is created so as to correspond to a chemical bond with an atom in another unit cell adjacent to the one unit cell containing the nodes A to I.

Here, as illustrated in FIG. 12, a loop edge extending on an upper side of the node A represents a loop edge identical to a loop edge extending downward of the node G. More specifically, for example, a loop edge connecting node A and node G corresponds to a virtual chemical bond between the node A in one unit cell and the node G in another unit cell adjacent to an upper side of the one unit cell.

Similarly, other loop edges illustrated in FIG. 12 individually represent loop edges corresponding to chemical bonds between atoms contained in the adjacent unit cell.

In this way, in the technique of treating the repeating structure of the crystal as a loop structure, by representing the chemical bonds between atoms in adjacent unit cells by loop edges, information on the repeating structure of the unit cell (information on how the unit cell is arranged) can be expressed without an increase in the number of nodes representing the unit cell.

That is, for example, in the technique of treating the repeating structure of the crystal as a loop structure, regarding the unit cell in the crystal, atoms in one unit cell that correspond to atoms in another unit cell adjacent to the one unit cell are specified, and expressed as a loop structure. By doing so, in the technique of treating the repeating structure of the crystal as a loop structure, the analysis (computation of a degree of similarity, and the like) targeted at the crystal can be performed with high accuracy since the repeating structure of the unit cell in the crystal can be appropriately expressed.

Here, when determining a degree of similarity between crystals having the repeating structure, it is desirable to obtain the degree of similarity by assuming a plurality of unit cells (multiplying the unit cell by an integer) as needed to reduce a difference between the numbers of atoms (numbers of nodes) included in the structures for which the degree of similarity is obtained.

In the following, a description will be given to a relationship between the number of atoms (number of nodes) included in the structures for which the degree of similarity is obtained and the degree of similarity value to be computed.

Figure 13A:
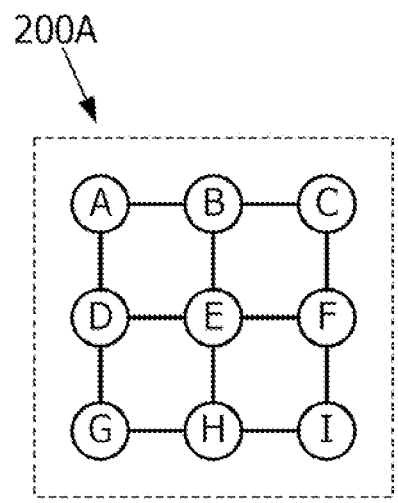
FIG. 13A is a diagram illustrating an example of a graph of a unit cell of a crystal.
Figure 13B:
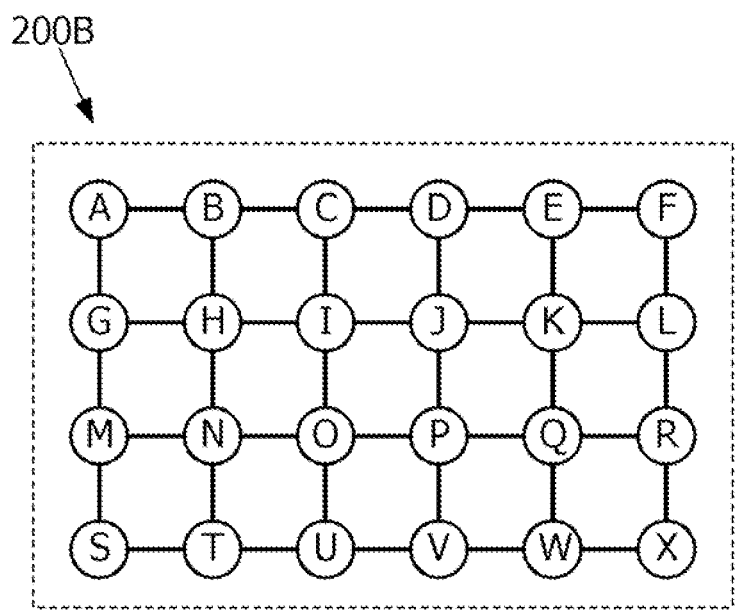
FIG. 13B is a diagram illustrating another example of a graph of a unit cell of a crystal.

First, a description is given to a case where the numbers of atoms (numbers of nodes) included in the structures for which the degree of similarity is obtained are significantly different. As illustrated in FIGS. 13A and 13B, assuming that a unit cell 200A has nine distinguishable types of atoms (atoms A to I), and a unit cell 200B has 24 distinguishable types of atoms (atoms A to X).

In a case where all atoms in the unit cell 200A of FIG. 13A have a common substructure with the atoms in the unit cell 200B of FIG. 13B (the unit cell 200A of FIG. 13A is included in the unit cell 200B of FIG. 13B), a degree of similarity of these structures is usually considered to be very large. However, when the degree of similarity is calculated on the basis of the equation of the degree of similarity described above, a numerical value of the degree of similarity of these structures is "0.675", which is not a large value.

From this fact, it can be seen that the degree of similarity is computed to be low due to a large difference in the number of nodes (number of atoms) included in the unit cell 200A in FIG. 13A and the unit cell 200B in FIG. 13B, and the accuracy of the analysis is low.

A degree of similarity S between a unit cell A and a unit cell B can be calculated by the following equation by simplifying the above equation of the degree of similarity.

$$S = \{N(A \cap B)/N(A) + N(A \cap B)/N(B)\} \times 0.5$$

Here, in the above equation, "$N(A \cap B) \leq N(A)$" and "$N(A \cap B) \leq N(B)$" are satisfied.

In the above equation, when "$N(A) \neq N(B)$" is satisfied, the degree of similarity S is not to be "1". Specifically, for example, when $N(A) = \lambda N(B)$ ($0 < \lambda \leq 1$) is satisfied, the maximum value that may be taken by the degree of similarity S is "$(1+\lambda)/2$". Furthermore, since a crystal can be considered as a periodic structure in which a unit cell is repeated in a semi-infinite manner, the fact that the degree of similarity S does not take the value of "1" due to the difference in the number of atoms (number of nodes) per unit cell is not to be said as an essential argument for the degree of similarity S of the crystal.

Here, as a technique of expressing, with 0 to 1, a value that may be taken by the degree of similarity S, for example, following two techniques can be exemplified.

Standardization of degree of similarity S

In standardizing the degree of similarity S, for example, a value that may be taken by the degree of similarity S ($0 \leq S \leq (1+\lambda)/2$) is set to 0 to 1, and standardized as a degree of similarity S' with the following equation.

$$S' = \{N(A \cap B)/N(A) + N(A \cap B)/N(B)\}/(1+\lambda)$$

Multiplying unit cell A and unit cell B by integer

By appropriately multiplying the unit cell A and the unit cell B by an integer and treating them as multiple cells, a difference between N(A) and N(B) is made as small as possible, and the value that may be taken by the degree of similarity S is set to 0 to 1.

In a case of standardizing the degree of similarity S, when $N(A) < N(B)$ is satisfied, even in a case of S'=1, there is a substructure B\A (a difference set obtained by subtracting an element of the unit cell A from the unit cell B) that is not included in "$A \cap B$".

In other words, for example, there may be a case of the degree of similarity S'=1 regardless of a structure of the substructure B\A and the number of atoms constituting each unit cell. As described above, the technique for standardizing the degree of similarity S is not suitable as a technique for evaluating a degree of similarity.

Whereas, in the technique of multiplying the unit cell A and the unit cell B by an integer, $N(A'') = N(B'')$ is set where, for example, A" is a structure of multiple cells of the unit cell A, and B″ is a structure of multiple cells of the unit cell B, and a degree of similarity S‴ is expressed by the following equation.

$$S''' = \{N(A'' \cap B'')/N(A'') + N(A'' \cap B'')/N(B'')\}/(1+\lambda)$$

However, in order to set N(A″)=N (B″), it may be necessary to increase the number of target unit cells (for example, adopting a least common multiple of unit cell A and unit cell B, or the like). In such a case, it is desirable to multiply at least one of the unit cell A or the unit cell B by an integer such that N(A″)≈N(B″) is satisfied, in other words, for example, so as to reduce a difference in the numbers of nodes of the structures for which the degree of similarity is calculated. As a specific guideline, in a case where N(A″)=λN(B″) is set, "9/10≤λ≤10/9" can be set. By defining in this way, it is possible to reduce a difference in the number of nodes included in the target structures, while suppressing the number of cells required as a target of the calculation of the degree of similarity, and the accuracy of the computed degree of similarity can be improved.

Here, a technique of multiplying the unit cell A and the unit cell B by an integer will be described with reference to FIGS. 14A to 14C.

Figure 14A:
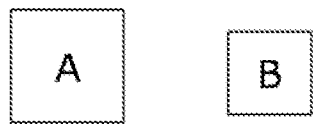
FIG. 14A is a diagram for explaining an example of a technique of multiplying a unit cell A and a unit cell B by an integer.
Figure 14B:
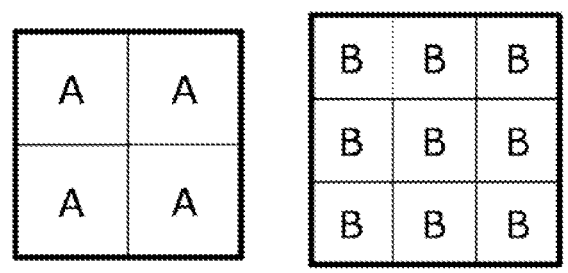
FIG. 14B is a diagram for explaining an example of the technique of multiplying the unit cell A and the unit cell B by an integer.
Figure 14C:
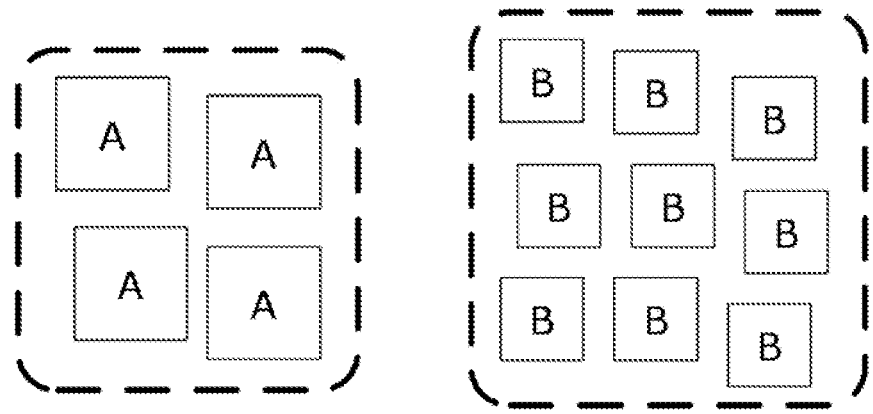
FIG. 14C is a diagram for explaining an example of the technique of multiplying the unit cell A and the unit cell B by an integer.

In the examples of FIGS. 14A to 14C, the unit cell A expressed as a graph with nodes and edges is referred to as a graph A, and the unit cell B expressed as a graph with nodes and edges is referred to as a graph B. In the technique of multiplying the unit cell A and the unit cell B by an integer, for example, in order to reduce a difference in the number of nodes in the graph A and the number of nodes in the graph B, at least one of the graph A or the graph B is replicated by multiplying by an integer. At this time, the replication is desirably performed, for example, in such a way as to minimize an absolute value of a difference between a total number of nodes in the graph A after the replication and a total number of nodes in the graph B after the replication.

Then, in this example, in the technique of multiplying the unit cell A and the unit cell B by an integer, for example, the graph A is replicated into four and the graph B is replicated into nine.

As for a graph obtained by integrating replicated graphs, for example, the graphs A may be bonded with each other, and the graphs B may be bonded with each other, as illustrated in FIG. 14B. Bonding here means providing an edge between individual graphs (between the graphs A or between the graphs B). Furthermore, in the graph obtained by integrating the replicated graphs, for example, as illustrated in FIG. 14C, bonding between the graphs A and between the graphs B need not be performed.

In this way, in the technique of multiplying the unit cell A and the unit cell B by an integer, for example, at least one of the graphs of the unit cells of two crystals is replicated. By replicating the graph so as to reduce the difference in the number of atoms (the number of nodes) between the two unit cells to be compared, it is possible to avoid a decrease in the degree of similarity caused by the difference in the number of atoms (the number of nodes). As a result, the accuracy of analysis (e.g., the degree of similarity) may be improved.

Here, in obtaining a degree of similarity between crystals, as described above, the number of atoms contained in each unit cell for which the structure is compared may increase (the number of bits required for computation of the degree of similarity may increase). In particular, for example, when the crystal is an ionic crystal, the unit cell contains a large number of anions (for example, oxygen atoms), and the number of atoms contained in the unit cell increases.

Figure 15A:
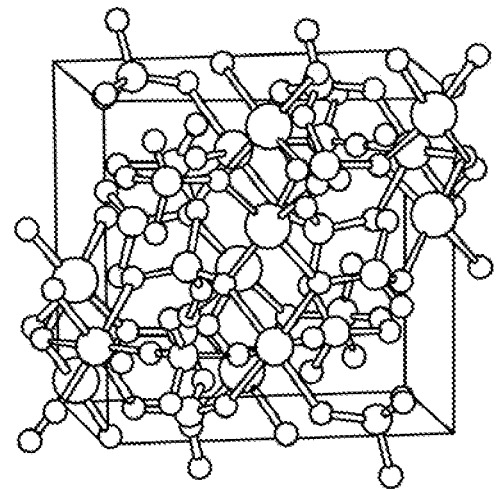
FIG. 15A is a diagram illustrating an example of a unit cell in an ionic crystal.
Figure 15B:
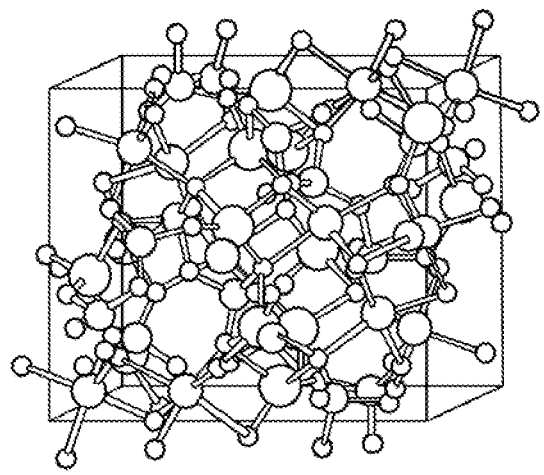
FIG. 15B is a diagram illustrating another example of a unit cell in an ionic crystal.

FIG. 15A illustrates an example of a unit cell in an ionic crystal. An ionic crystal A illustrated in FIG. 15A has eight pieces of lithium (Li), four pieces of manganese (Mn), 16 pieces of phosphorus (P), and 48 pieces of oxygen (O) individually in the unit cell, and has a total of 76 atoms. Likewise, FIG. 15B illustrates another example of a unit cell in an ionic crystal. An ionic crystal B illustrated in FIG. 15B has 16 pieces of lithium (Li), eight pieces of manganese (Mn), 16 pieces of phosphorus (P), and 56 pieces of oxygen (O) individually in the unit cell, and has a total of 96 atoms.

In the examples illustrated in FIGS. 15A and 15B, in a case of calculating a degree of similarity between the ionic crystal A and the ionic crystal B, for example, a node of the conflict graph described above is created for every type of each atom. At this time, the number of nodes of the conflict graph (the number of bits required for calculation) is "8×16=128" for lithium, "4×8=32" for manganese, "16× 16=256" for phosphorus and "48×56=2688" for oxygen. Therefore, in order to calculate the degree of similarity between the ionic crystal A and the ionic crystal B, for example, the number of nodes in the conflict graph (the number of bits required for the calculation) is to be "128+ 32+256+2688=3104".

In this way, when the number of atoms (number of nodes) contained in the unit cell increases, it has been difficult to compute a degree of similarity assuming multiple unit cells, due to a limit on the number of bits that can be handled by an annealing machine used for computation of the degree of similarity. For example, the number of bits that can be used in the annealing machine is at most about 8,000 bits, and it has been difficult to handle the unit cell by multiplying by an integer due to lack of available bits in a case where 3,000 bits or more are required even in comparing unit cells as in the example described above.

As described above, in the related art, when the number of atoms contained in the unit cell of the ionic crystal is large in analyzing an ionic crystal, there has been a problem that the number of bits required for calculation increases and accurate analysis may be difficult.

Therefore, the present inventor has diligently studied a method and the like capable of reducing (suppressing) the number of bits required for analysis on an ionic crystal, and obtained the following findings.

In other words, for example, the present inventor has found that the number of bits required for analysis on an ionic crystal can be reduced (suppressed) by the following crystal analysis method and the like.

A crystal analysis method as an example of the technology disclosed in the present application includes:

a graph creation process of creating a graph in which one repeating unit cell is extended to an adjacent repeating unit cell adjacent to the one repeating unit cell, in which the one repeating unit cell contains an intra-cell node that indicates data of an atom in the one repeating unit cell and an intra-cell edge that indicates data of a chemical bond between two atoms in the one repeating unit cell, in a crystal; and an analysis process of analyzing a crystal by using the graph, in which in the graph creation process, in a case where the crystal is an ionic crystal, in the ionic crystal, when a number of the intra-cell nodes that are data of an anionic atom bonded to a cationic atom in the one repeating unit cell is n, a number of the intra-cell nodes that are data of the anionic atom is set to be n−1 or less.

Here, in an example of the technology disclosed in the present application, in the graph creation process, for example, there is prepared one repeating unit cell containing an intra-cell node that indicates data of an atom in the one repeating unit cell and an intra-cell edge that indicates data of a chemical bond between two atoms in the one repeating unit cell. That is, for example, in an example of the technology disclosed in the present application, for example, in order to express atoms of the unit cell in a crystal and a chemical bond between the atoms, the one repeating unit cell (a graph of the unit cell) described above including the intra-cell node and the intra-cell edge is prepared.

Then, in an example of the technology disclosed in the present application, in the graph creation process, for example, a graph is created in which the one repeating unit cell is extended to an adjacent repeating unit cell adjacent to the one repeating unit cell, in the graph creation process. That is, for example, in an example of the technology disclosed in the present application, for example, in order to express a repeating structure (periodic structure, crystalline structure) of an ionic crystal, a graph is created in which the one repeating unit cell is extended in consideration of a relationship with atoms of a surrounding repeating unit cell. By doing so, in an example of the technology disclosed in the present application, the repeating structure in the crystal can be appropriately expressed, and the crystal can be analyzed with high accuracy.

Moreover, in an example of the technology disclosed in the present application, in the graph creation process, for example, in a case where the crystal is an ionic crystal, in the ionic crystal, when a number of the intra-cell nodes that are data of an anionic atom bonded to a cationic atom in the one repeating unit cell is n, a number of the intra-cell nodes that are data of the anionic atom is set to be n−1 or less. In other words, in the graph creation process, for example, by not considering (by deleting) at least one of anionic atoms contained in the one repeating unit cell as a node, the cationic atom and the anionic atom are collectively regarded as one node.

By doing so, in an example of the technology disclosed in the present application, since the number of intra-cell nodes in the one repeating unit cell can be suppressed (reduced), the number of bits required for calculation can be reduced (suppressed). That is, for example, in an example of the technology disclosed in the present application, by creating a graph in which at least some nodes of anionic atoms in the ionic crystal are deleted, the number of nodes included in the graph (the number of bits required for calculation) can be suppressed.

Subsequently, in an example of the technology disclosed in the present application, in the analysis process, for example, the crystal is analyzed using the graph created in the graph creation process. That is, for example, in an example of the technology disclosed in the present application, in the analysis process, for example, the ionic crystal is analyzed on the basis of the graph in which at least some nodes of the anionic atoms in the ionic crystal are deleted.

By doing so, in an example of the technology disclosed in the present application, a graph in which the number of intra-cell nodes is suppressed is used, so that, for example, it is possible to perform highly accurate analysis, such as calculating a degree of similarity after multiplying the unit cell by an integer to make the number of nodes uniform.

Here, in the graph created in the graph creation process, the number of intra-cell nodes that are data of an anionic atom is not particularly limited as long as it is n−1 or less as described above, and can be appropriately selected depending on a purpose, but desirably set to "0 (zero)", for example. In other words, for example, in an example of the technology disclosed in the present application, it is desirable not to consider all anionic atoms contained in one repeating unit cell as nodes (to remove all anions).

A description will be given to a form in which the number of intra-cell nodes that are data of an anionic atom is set to "0" in the graph created in the graph creation process with reference to FIG. 16.

Figure 16:
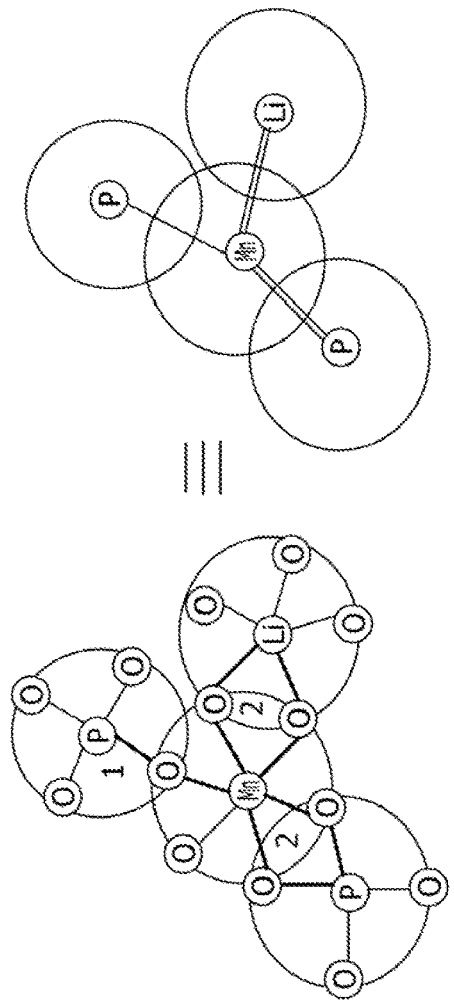
FIG. 16 is a diagram illustrating an example of a related art and one embodiment of the present application in comparison.
Figure 16:
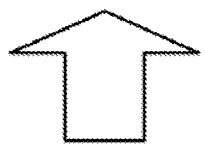
Figure 16:
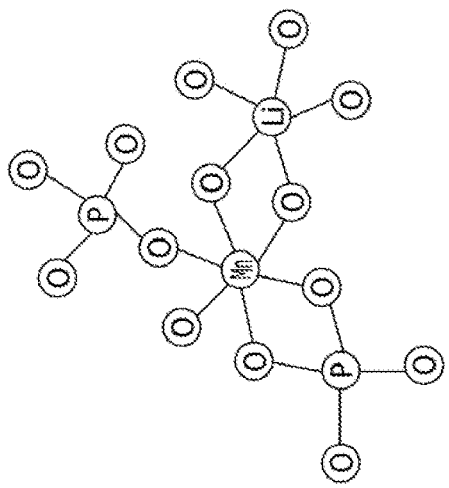

FIG. 16 illustrates an example in which one repeating unit cell in an ionic crystal contains one piece each of lithium (Li), manganese (Mn), and phosphorus (P), and 14 pieces of oxygen (O). As illustrated in an example of the related art in FIG. 16, in an ionic crystal, pieces of oxygen of the number corresponding to a valence is individually bonded in a single bond to each piece of cationic atom (lithium, manganese, and phosphorus). In this way, in an ionic crystal, a cationic atom and an anionic atom are usually bonded to each other. In an example of the related art, a graph is created while regarding each of these atoms as a node, and an interatomic bond as an edge of a single bond.

Furthermore, in the example illustrated in FIG. 16, for example, between phosphorus (P) positioned at a lower left of the unit cell and manganese (Mn), there are two bonds via oxygen (O), and phosphorus (P)) positioned on an upper side of the unit cell and manganese (Mn are bonded to each other via one single-bonded oxygen (O). Moreover, in the example illustrated in FIG. 16, for example, manganese (Mn) and lithium (Li) are bonded to each other via two pieces of single-bonded oxygen (O).

Then, as illustrated in one embodiment of the present application in FIG. 16, in an example of the technology disclosed in the present application, a cationic atom (+) and an anionic atom (−) surrounding the cationic atom are collectively treated as one node. That is, for example, as illustrated in one embodiment of the present application in FIG. 16, in an example of the technology disclosed in the present application, for example, the number of nodes contained in the unit cell can be reduced by considering only the cationic atom as a node without considering the anionic atom as a node.

Furthermore, in an example of the technology disclosed in the present application, a bond order between cationic atoms can be set to the number of chemical bonds via anions that are considered to be non-existent between the cationic atoms (the number of anions deleted between the cations). In other words, for example, in an example of the technology disclosed in the present application, a bond order between cationic atoms can be determined with the number of bonds between cationic atoms via anionic atoms.

For example, in the example illustrated in FIG. 16, for example, a bond order between phosphorus (P) positioned at a lower left of the unit cell and manganese (Mn) can be set to "2", while a bond order between phosphorus (P) positioned on an upper side of the unit cell and manganese (Mn) can be set to "1". Moreover, in the example illustrated in FIG. 16, for example, a bond order between manganese (Mn) and lithium (Li) can be set to "2".

In an example of the technology disclosed in the present application, as illustrated in one embodiment of the present application in FIG. 16, for example, the number of nodes contained in the unit cell can be reduced by considering only the cationic atom as a node without considering the anionic atom as a node. In an example illustrated in FIG. 16, the number of nodes contained in the unit cell is 17 in the example of the related art, but the number of nodes contained in the unit cell can be reduced to 4 in one embodiment of the present application.

Thus, in an example of the technology disclosed in the present application, the number of nodes contained in the unit cell can be suppressed by regarding the cationic atom and the anionic atom collectively as one node, by deleting at least some anionic atoms contained in the unit cell to handle.

Therefore, in an example of the technology disclosed in the present application, the number of nodes included in the graph used for analysis on the ionic crystal, in other words, for example, the number of bits required for calculation can be reduced (suppressed).

In the following, each process in the crystal analysis method disclosed in the present application will be described in detail.

The crystal analysis method disclosed in the present application includes, for example, the graph creation process and the analysis process, and further includes other processes, as needed.

<Graph Creation Process>

In the graph creation process in an example of the technology disclosed in the present application, as described above, there is prepared one repeating unit cell containing an intra-cell node that indicates data of an atom in the one repeating unit cell and an intra-cell edge that indicates data of a chemical bond between two atoms in the one repeating unit cell. Then, in the graph creation process, a graph is created in which the one repeating unit cell is extended to an adjacent repeating unit cell adjacent to the one repeating unit cell, in the graph creation process.

<<Graph>>

In an example of the technology disclosed in the present application, a graph has, for example, a node that is data on an atom, and an edge that is data on a chemical bond between two atoms.

Here, in an example of the technology disclosed in the present application, the graph can be, for example, an abstract data type including a group of nodes (vertices) and a group of edges (branches) representing a connection relationship between the nodes. The graph is represented by $G=(V, E)$, for example, where V is a set of nodes and E is a set of edges. V is a finite set, and E is a set of sets including two elements selected from V.

The node can be assumed to indicate an atom in one unit cell of a crystal. Hereinafter, the node indicating an atom in one unit cell of a crystal may be referred to as an "intra-cell node".

Furthermore, the edge can be assumed to represent a chemical bond between atoms in a unit cell. Hereinafter, the edge indicating a chemical bond between atoms in a unit cell may be referred to as "intra-cell edge".

The graph may have a node (hereinafter sometimes referred to as an "extension node") indicating an atom in an adjacent unit cell that is adjacent to a repeating unit cell, in which the atom has a chemical bond with an atom in the repeating unit cell.

In this case, the graph may have an edge (hereinafter sometimes referred to as an "extension edge") indicating a chemical bond between an atom corresponding to the intra-cell node and an atom corresponding to the extension node. Moreover, in this case, the graph may have an edge (hereinafter sometimes referred to as an "edge between extension nodes") indicating a chemical bond between two atoms corresponding to extension nodes.

That is, for example, in an example of the technology disclosed in the present application, a graph created in the graph creation process desirably includes:

the intra-cell node that indicates data of an atom in one repeating unit cell, and the intra-cell edge that indicates data of a chemical bond between two atoms in a unit cell; and the extension node that is data of an atom, in which the atom has a chemical bond with an atom in the one repeating unit cell and is in an adjacent repeating unit cell adjacent to the one repeating unit cell, and the extension edge that is data of a chemical bond between an atom corresponding to the intra-cell node in the one repeating cell unit and an atom corresponding to the extension node.

In this way, in an example of the technology disclosed in the present application, the technique described with reference to FIG. 11 in which the unit cell is extended and handled by using the extension nodes can be suitably used.

Furthermore, the graph may have an edge indicating a virtual chemical bond between an atom X in a unit cell and an atom Y being in the unit cell and corresponding to an atom Y' that has a chemical bond with the atom X in the unit cell and is in an adjacent unit cell adjacent to the unit cell. Here, the atom Y being in the unit cell and corresponding to the atom Y' in the adjacent unit cell means an atom in the unit cell that overlaps with the atom Y' in the adjacent unit cell when the adjacent unit cell and the unit cell are overlapped so that constituent atoms overlap.

Note that, in the following, an edge indicating a virtual chemical bond between the atom Y in the unit cell described above and the atom X in the unit cell may be referred to as a "loop edge".

That is, for example, in an example of the technology disclosed in the present application, a graph created in the graph creation process is desirably a loop graph that includes:

an intra-cell node that indicates data of an atom in one repeating unit cell, and an intra-cell edge that indicates data of a chemical bond between two atoms in a unit cell; and a loop edge that indicates data of the chemical bond that is virtual between an atom X and an atom Y that is in the one repeating unit cell and corresponds to an atom Y', in which the atom Y' has the chemical bond with the atom X in the one repeating cell unit and is in an adjacent repeating unit cell adjacent to the one repeating unit cell.

In this way, in an example of the technology disclosed in the present application, the technique of treating the repeating structure of the crystal as a loop structure described with reference to FIG. 12 can be suitably used.

Intra-cell nodes and extension nodes have data such as an atom type, an atom valence, and an atom charge, for example.

Intra-cell edges, loop edges, and extension edges have data such as a bond type, a bond angle, a bond distance, and a bond order, for example. The bond angle and the bond distance can be expressed using, for example, coordinate data of an atom or a chemical bond.

Furthermore, intra-cell edges, loop edges, and extension edges are desirably created by, for example, Voronoi tessellation between nodes.

Voronoi tessellation is a technique of dividing the nearest neighbor region of each node by drawing a perpendicular bisector on a straight line connecting adjacent nodes.

Here, a Voronoi diagram and Voronoi tessellation will be described.

A Voronoi diagram is a diagram in which, with a plurality of points (generators) arranged at any positions in a certain metric space, a region is divided on the basis of to which generator other points in an identical metric space are closest. Furthermore, this division of the region is called Voronoi tessellation. In the Voronoi diagram, a division pattern is determined only by a position of the generator.

In a case where a unit cell of a crystal is schematically represented including chemical bonds, the chemical bonds in the unit cell of the crystal are usually not uniquely determined. However, creating edges (intra-cell edges, loop edges, and extension edges) by Voronoi tessellation makes it possible to uniquely determine edges (intra-cell edges, loop edges, and extension edges). As a result, it is possible to uniquely determine edges for a plurality of crystals, and this can improve an accuracy of analysis of crystals.

Furthermore, intra-cell edges, loop edges, and extension edges can be created, for example, on the basis of a standard ionic radius of an atom. For example, it is possible to apply a rule in which an edge between nodes is created if "d≤a (r1+r2)+b" is satisfied, where d is a distance between any two nodes, and r1 and r2 are the ionic radii of the individual nodes. Here, a is a constant equal to or larger than 0, and b is a constant. Furthermore, 1.0≤a≤1.2 and 0 Å≤b≤0.4 Å are desirable.

As a method for creating intra-cell edges, loop edges, and extension edges, it is possible to freely select one or both of the two techniques described above, for example, the Voronoi tessellation technique and the technique using the standard ionic radius. In a case where both are selected, for example, among intra-cell edges, loop edges, and extension edges that can be determined by Voronoi tessellation, those that are regarded as intra-cell edges, loop edges, and extension edges in the technique using the standard ionic radius of the atom may be created as intra-cell edges, loop edges, and extension edges.

Moreover, in an example of the technology disclosed in the present application, as described above, in the graph creation process, in a case where the crystal is an ionic crystal, in the ionic crystal, when the number of intra-cell nodes that are data of an anionic atom bonded to a cationic atom in one repeating unit cell is n, the number of intra-cell nodes that are data of the anionic atom is set to be n−1 or less.

Here, the ionic crystal means, for example, a crystal formed by ionic bonding of a cation (a positive ion, cationic atom) and an anion (a negative ion, anionic atom). In an example of the technology disclosed in the present application, the ionic crystal to be analyzed is not particularly limited, and can be appropriately selected depending on a purpose.

Furthermore, in an example of the technology disclosed in the present application, as described above, it is desirable not to consider all anionic atoms contained in a repeating unit cell as nodes (to remove all anions). In other words, for example, in an example of the technology disclosed in the present application, it is desirable to set the node of the anionic atom to "0" and consider that all the cationic atoms are directly bonded to each other.

More specifically, for example, in an example of the technology disclosed in the present application, it is desirable that the number of intra-cell nodes that are data of an anionic atom is set to 0 in the graph creation process. By doing so, the number of nodes contained in the repeating unit cell can be further reduced, and the number of bits required for the analysis of the ionic crystal can be further suppressed.

Note that, in the graph creation process, when the number of intra-cell nodes that are data of an anionic atom is not set to 0 (when some of all anionic atoms contained in the repeating unit cell are left), the anionic atom to be regarded as the intra-cell node can be appropriately selected depending on a purpose.

In an example of the technology disclosed in the present application, it may be determined whether or not to consider as the intra-cell node (whether or not to delete), for example, from a bonding relationship between individual anionic atoms in the repeating unit cell, and the like. In this case, for example, the anionic atom bonded to two or more cationic atoms may be deleted, while the anionic atom bonded to only one cationic atom is left.

Furthermore, in an example of the technology disclosed in the present application, anionic atoms that are not regarded as the intra-cell nodes (anionic atoms to be deleted) are not particularly limited, and can be appropriately selected depending on a purpose. Examples thereof include an oxygen atom, a chlorine atom, a fluorine atom, and the like, for example.

Anionic atoms that are not regarded as the intra-cell nodes can be appropriately selected in accordance with the ionic crystal to be analyzed. Then, the number of bits required for calculation can be further suppressed, for example, by selecting an anionic atom having a large number of atoms, in the ionic crystal.

In an example of the technology disclosed in the present application, a bond order between cationic atoms when the anionic atom is deleted can be set to, for example, the number of chemical bonds via anions that are considered to be non-existent between the cationic atoms. In other words, for example, in an example of the technology disclosed in the present application, a bond order between cationic atoms can be determined with the number of bonds between cationic atoms via anionic atoms, as described above.

That is, for example, in an example of the technology disclosed in the present application, in the graph creation process, when the number of intra-cell nodes that are data of an anionic atom is set to 0, and it is considered that cationic atoms in one repeating unit cell are directly chemically bonded to each other, a bond order of a chemical bond between the cationic atoms is desirably set to the number of chemical bonds between the cationic atoms via the anionic atom considered to be non-existent.

By doing so, in an example of the technology disclosed in the present application, as illustrated in FIG. 16, a bonding state of each atom in the ionic crystal can be considered more appropriately, and more highly accurate analysis can be performed.

<Analysis Process>

In the analysis process in an example of the technology disclosed in the present application, a crystal analysis is performed by using a graph created in the graph creation process as described above.

The crystal analysis performed in the analysis process is not particularly limited, and can be appropriately selected depending on a purpose. Examples thereof include analysis of structural similarity of a plurality of crystals, prediction of crystal characteristics, and the like, for example.

A technique for analyzing similarity of structures (crystalline structures) of a plurality of crystals is not particularly limited and can be appropriately selected depending on a purpose, as long as the technique is for analyzing similarity between a crystalline structure of a certain crystal and a crystalline structure of another crystal by using a graph created in the graph creation process. Examples of the technique for analyzing similarity of structures of a plurality of crystals include a technique of computing a score of a degree of similarity and determining a higher similarity as the score is larger, and the like, for example.

The method of computing a score for the degree of similarity is not particularly limited and can be appropriately selected depending on a purpose, and there are the following techniques (1) and (2), and the like, for example.

Technique (1), fingerprint method

Technique (2), a technique to analyze similarity of structures by searching for a common substructure by expressing a maximum independent set problem of a conflict graph with an Ising model equation and solving with an annealing machine or the like.

In the fingerprint method as the technique (1), for example, whether or not a substructure in a reference structure is included in a structure to be compared is represented by 0 or 1, and the degree of similarity is evaluated.

Furthermore, as the technique using the conflict graph as the technique (2), the technique described with reference to FIGS. 1 to 9 can be suitably used. Note that details of analysis on the degree of similarity by using the conflict graph in an example of the technology disclosed in the present application will be described later.

Note that the technique of computing a score for the degree of similarity is not limited to these techniques. For example, the score for the degree of similarity may be computed on the basis of a cosine degree of similarity, a correlation coefficient, a correlation function, an edit distance (also referred to as a Levenshtein distance), or the like related to calculation of the degree of similarity.

The technique of predicting characteristics of a crystal is not particularly limited and can be appropriately selected depending on a purpose, as long as it is a technique of predicting characteristics of a crystal by using a graph created by the graph creation process. Examples thereof include prediction of characteristics by using a learning model, and the like, for example.

Examples of the prediction of characteristics by using a learning model include a technique of creating a learning model by machine learning and predicting characteristics of a crystal by using the learning model, and the like, for example.

Examples of machine learning include supervised learning, unsupervised learning, and the like, for example. The learning technique in a case where a learning model is created by machine learning is not particularly limited and can be appropriately selected depending on a purpose. In a case of supervised learning, for example, it is possible to use a technique of performing learning by using a training data set including a graph of a crystal and characteristics of the crystal as a label.

As the training data in machine learning, for example, one having a graph created in the graph creation process and data on the characteristics of the crystal corresponding to the graph can be used.

Furthermore, the characteristics to be predicted are not particularly limited and can be appropriately selected depending on a purpose, and may be chemical characteristics or physical characteristics. Specific examples of the characteristics include electrical conductivity, ionic conductivity, discharge potential, relative permittivity, thermal conductivity, specific heat, and the like, for example.

Furthermore, in predicting the characteristics, the graph (graph structure data) created in the graph creation process may be processed and used. For example, a graph may be converted into a tensor so that graph structure data may be learned with high accuracy by using machine learning (e.g., deep learning) technology.

Here, the tensor means data expressed as a multidimensional array in which concepts such as matrices and vectors have been commonalized.

In an example of the technology disclosed in the present application, as described above, it is desirable to compute the degree of similarity in the ionic crystal in the analysis process.

That is, for example, in an example of the technology disclosed in the present application, it is desirable to create a first graph for a first crystal and a second graph for a second crystal in the graph creation process, and compute the degree of similarity between the first crystal and the second crystal on the basis of the first graph and the second graph in the analysis process.

Moreover, in an example of the technology disclosed in the present application, as described above, when computing the degree of similarity, it is desirable to obtain the degree of similarity by assuming a plurality of unit cells (multiplying the unit cell by an integer) as needed so as to reduce a difference in the numbers of atoms (numbers of nodes) included in the structures for which the degree of similarity is to be obtained.

That is, for example, in an example of the technology disclosed in the present application, it is desirable to perform computation of the degree of similarity in the analysis process after at least one of one repeating unit cell for the first graph or one repeating unit cell for the second graph is multiplied by an integer such that the numbers of intra-cell nodes in the first and second graphs are approximated.

By doing so, in an example of the technology disclosed in the present application, by reducing a difference in the number of atoms (number of nodes) of two repeating unit cells for which structures are compared, it is possible to avoid a decrease in the degree of similarity due to a difference in the number of atoms, and it is possible to further improve the accuracy of a computation result of the degree of similarity.

Furthermore, in an example of the technology disclosed in the present application, as described above, it is desirable to compute the degree of similarity in the analysis process by solving a maximum independent set problem of a conflict graph. By solving the maximum independent set problem of the conflict graph, as a technique for computing the degree of similarity between the first crystal and the second crystal, the technique described with reference to FIGS. 1 to 9 can be suitably used.

In the conflict graph used for computation of the degree of similarity between the first crystal and the second crystal, for example, a combination of each node atom constituting a repeating unit cell of the first crystal expressed as a graph and each node atom constituting a repeating unit cell of the second crystal expressed as a graph is defined as a node.

Here, in an example of the technology disclosed in the present application, the case where "two nodes are compared and are identical to each other" means that, when two nodes are compared, these nodes are constituted by node atoms in identical situations (bonding situations) to each other. Likewise, in an example of the technology disclosed in the present application, the case where "two nodes are compared and are not identical to each other" means that, when two nodes are compared, these nodes are constituted by node atoms in different situations (bonding situations) from each other.

More specifically, for example, in an example of the technology disclosed in the present application, for example, the computation of the degree of similarity in the analysis process is desirably worked out by searching for the maximum independent set of the conflict graph between the first graph and the second graph by using the following Equation (1). Furthermore, the following Equation (1) is an equation used when the number of intra-cell nodes that are data of an anionic atom is set to 0 in the graph creation process.

[Formula 6]

$$E = -\alpha \sum_i x_i + \beta \sum_i \sum_j c'_{i,j} x_i x_j \qquad \text{EQUATION (1)}$$

Here, in Equation (1), E is a Hamiltonian in which minimizing E means searching for the maximum independent set, $c'_{ij}$ is a coefficient representing a weight regarding a bond order between the i-th node and the j-th node in the conflict graph between the first graph and the second graph, $x_i$ is a binary variable representing that the i-th node has 0 or 1, $x_j$ is a binary variable representing that the j-th node has 0 or 1, and $\alpha$ and $\beta$ are positive numbers.

Here, $c'_{ij}$ in the above Equation (1) will be described in detail.

First, as described above, in an example of the technology disclosed in the present application, a bond order between cationic atoms when anionic atoms are deleted can be determined with, for example, the number of bonds between cationic atoms via anionic atoms.

Therefore, the bond order between cationic atoms is determined with a combination of cationic atoms, and thus can be incorporated as a weight in a penalty term (term whose coefficient is $\beta$) of the Ising model equation (Equation (1)) for solving the maximum independent set problem of the conflict graph. That is, for example, in an example of the technology disclosed in the present application, by expressing the bond order between cationic atoms as the weight ($c'_{ij}$) in the penalty term of the Ising model equation, the degree of similarity can be calculated in consideration of the bond order between cationic atoms.

For example, $c'_{ij}$ representing the weight regarding the bond order between cationic atoms can be determined by, for example, the following rule.

Between a combination of atoms in the i-th node and a combination of atoms in the j-th node, in a case where there is no bond, "$c'_{ij}=0$" is set.

Between a combination of atoms in the i-th node and a combination of atoms in the j-th node, in a case where there is a bond in only one atom combination, "$c'_{ij}=\lambda_1$" is set.

Between a combination of atoms in the i-th node and a combination of atoms in the j-th node, in a case where there is a bond in both atom combinations, "$c'_{ij}=\lambda_2 (1-\min\{c_1/c_2, c_2/c_1\})$" is set.

Here, $\lambda_1$ and $\lambda_2$ are positive constants, and it is usually desirable that $\lambda_1=\lambda_2=1$ is set. Note that, in the following description, a case of $\lambda_1=\lambda_2=1$ will be described as an example.

Note that min {A, B} means that a smaller value from among A and B is selected. Moreover, $c_1$ means a bond order between an atom of the i-th node and an atom of the j-th node in the first graph, and $c_2$ means a bond order between an atom of the i-th node and an atom of the j-th node in the second graph.

FIG. 17 illustrates an example of a relationship between a combination of nodes in the first graph and the second graph and $c'_{ij}$, which represents a weight regarding a bond order between cationic atoms.

As illustrated in FIG. 17, according to the rules for $c'_{ij}$, which represents a weight regarding a bond order, for example, in a case where there is no bond between a node A1 and a node A2 in the first graph and between a node B1 and a node B2 in the second graph, $c'_{ij}$ is to be "0". That is, for example, in this case, since these nodes are constituted by atoms that are in situations (bonding situations) identical to each other (bonding situations are not contradicted), $c'_{ij}$ is to be "0" so that a value of a penalty term whose coefficient is $\beta$ is "0".

Likewise, in a case where there are bonds of the same bond order between the node A1 and the node A2 in the first graph and between the node B1 and the node B2 in the second graph, (in the example of FIG. 17, in a case where both have a bond order of 1), $c'_{ij}$ is to be "0".

Moreover, as illustrated in FIG. 17, according to the rules for $c'_{ij}$, for example, in a case where there is a bond between the node A1 and the node A2 in the first graph, and there is no bond between the node B1 and the node B2 in the second graph, $c'_{ij}$ is to be "1". That is, for example, in this case, these nodes are constituted by atoms that are in completely different situations (bonding situations) from each other (bonding situations are completely contradicted), $c'_{ij}$ is to be "1" so that the penalty term whose coefficient is $\beta$ becomes a large value.

Furthermore, as illustrated in FIG. 17, according to the rules for $c'_{ij}$, for example, in a case where there are bonds with bond orders different from each other between the node A1 and the node A2 in the first graph and between the node B1 and the node B2 in the second graph, $c'_{ij}$ is to be a "number between 0 and 1" according to the bond order. That is, for example, in this case, these nodes have no contradiction in terms of bonding, but will be constituted by atoms that are in mutually different situations (bonding situations) to some extent since the bond order is different. Therefore, $c'_{ij}$ is to be "a number between 0 and 1" so that a value of the penalty term whose coefficient is $\beta$ is a value according to the bond order.

Thus, in an example of the technology disclosed in the present application, $c'_{ij}$ representing a weight regarding a bond order can be a multi-valued weight according to a bond order (a weight according to a difference in the bond order), rather than a weight (binary of 0 or 1) in consideration of only whether or not there is a bond between nodes. By doing so, in an example of the technology disclosed in the present application, the degree of similarity can be calculated with higher accuracy in consideration of the bond order between the cationic atoms.

Note that, in the description described above, the case of $\lambda_1=\lambda_2=1$ has been described as an example, but the technology disclosed in the present application is not limited to this, and $\lambda_1$ and $\lambda_2$ can be set to positive constants other than 1, as needed.

In an example of the technology disclosed in the present application, when a search for the maximum independent set is performed using the above Equation (1), it is not highly prioritized to create the conflict graph, and it suffices that at least the above Equation (1) can be minimized. In other words, for example, in an example of the technology disclosed in the present application, the search for the maximum independent set in the conflict graph is replaced with a combination optimization problem in a Hamiltonian in which minimizing means the searching for the maximum independent set, and solved. Here, the minimization of the Hamiltonian represented by the Ising model equation in the QUBO format as in the above Equation (1) can be executed in a short time by performing the annealing method (annealing) using an annealing machine or the like.

Therefore, in the technology disclosed in the present application, in one aspect, by using the above Equation (1), the maximum independent set can be searched by an annealing method using an annealing machine or the like, so that the degree of similarity of a crystal can be computed in a shorter time. In other words, for example, in the technology disclosed in the present application, in one aspect, the degree of similarity of the crystal can be computed in a shorter time by searching for the maximum independent set by minimizing the Hamiltonian (H) in the above Equation (1) by the annealing method. Note that details of the annealing method will be described later.

Here, the annealing machine is not particularly limited and can be appropriately selected depending on a purpose, as long as the annealing machine is a computer that employs an annealing method of searching for a ground state for an energy function represented by an Ising model. Examples of the annealing machine include a quantum annealing machine, a semiconductor annealing machine using a semiconductor technology, a machine that performs simulated annealing executed by software using a central processing unit (CPU) or a graphics processing unit (GPU), and the like, for example. Furthermore, for example, a digital annealer (registered trademark) may be used as the annealing machine.

Furthermore, in the example described above, a description has been given to the equation when the number of intra-cell nodes that are data of an anionic atom is set to 0. However, when the number of intra-cell nodes that are data of an anionic atom is not set to 0 (some anionic atoms are left), for example, the following equation can be used.

[Formula 7]

$$E = -\alpha \sum_i c''_i x_i + \beta \sum_i \sum_j c'_{i,j} x_i x_j$$

Here, in the above Equation (1), E is a Hamiltonian in which minimizing E means searching for the maximum independent set, $c''_i$ is a coefficient representing a weight in the i-th node in the conflict graph between the first graph and the second graph, $c'_{ij}$ is a coefficient representing a weight regarding a bond order between the i-th node and the j-th node in the conflict graph between the first graph and the second graph, $x_i$ is a binary variable representing that the i-th node has 0 or 1, $x_j$ is a binary variable representing that the j-th node has 0 or 1, and $\alpha$ and $\beta$ are positive numbers.

In the above equation, "$c''_i$" is introduced for Equation (1), and "a combination of the same anionic atoms" can be added to the nodes of the graph by introducing this "$c''_i$".

Here, "$c''_i$" can be a constant involved in selection of a combination of the i-th node in the conflict graph between the first graph and the second graph. More specifically, for example, when a constant for a combination between cationic atoms is assumed to be "$c''_j$" and a constant for a combination between anionic atoms is assumed to be "$c''_k$", then "$c''_j \geq c''_k \geq 0$" can be set.

This is because, since the number of anionic atoms is reduced in an example of the technology disclosed in the present application, it is not essential that a computation result of the degree of similarity is affected by the selection of anionic atoms to be deleted.

Moreover, in an example of the technology disclosed in the present application, similarly to the technique described with reference to FIGS. 1 to 9, the degree of similarity related to the characteristics of the searched maximum independent set can be obtained by using the following Equation (2). In other words, for example, in an example of the technology disclosed in the present application, it is desirable that the computation of the degree of similarity in the analysis process is worked out for the searched maximum independent set by using the following Equation (2).

[Formula 8]

EQUATION (2)

$$S(G_A, G_B) = \delta \max\left\{\frac{|V_C^A|}{|V_A|}, \frac{|V_C^B|}{|V_B|}\right\} + (1-\delta)\min\left\{\frac{|V_C^A|}{|V_A|}, \frac{|V_C^B|}{|V_B|}\right\}$$

In the above Equation (2), $S(G_A, G_B)$ represents a degree of similarity between the first crystal represented as the first graph and the second crystal represented as the second graph, is represented by 0 to 1, and means a higher degree of similarity as approaching to 1, $V_A$ represents a total number of node atoms in the first crystal represented as the first graph, $V_C^A$ represents the number of node atoms included in the maximum independent set of the conflict graph among node atoms in the first crystal represented as the first graph, and $V_B$ represents a total number of node atoms in the second crystal represented as the second graph, $V_C^B$ represents the number of node atoms included in the maximum independent set of the conflict graph among node atoms in the second crystal represented as the second graph, and $\delta$ is a number from 0 to 1.

<Other Processes>

Other processes are not particularly limited and can be appropriately selected depending on a purpose.

(Crystal Analysis Device)

The crystal analysis device disclosed in the present application can be, for example, a device that executes the crystal analysis method disclosed in the present application. Furthermore, a suitable mode in the crystal analysis device disclosed in the present application can be made similar to a suitable mode in the crystal analysis method disclosed in the present application, for example.

Here, the crystal analysis device disclosed in the present application has the graph creation unit and the analysis unit, and may further have other units (sections) as needed. Note that the graph creation unit and the analysis unit can be implemented by, for example, a combination of a processor such as a central processing unit (CPU) and a memory such as a random access memory (RAM), or as a part of an annealing machine.

(Crystal Analysis Program)

The crystal analysis program disclosed in the present application can be, for example, a program that causes a computer to execute the crystal analysis method disclosed in the present application. Furthermore, a suitable mode of the crystal analysis program disclosed in the present application can be made similar to a suitable mode of the crystal analysis method disclosed in the present application, for example.

The crystal analysis program disclosed in the present application can be created using various known programming languages in accordance with a configuration of a computer system to be used, a type and a version of an operating system, and the like.

The crystal analysis program disclosed in the present application may be recorded in a recording medium such as an internal hard disk or an external hard disk, or may be recorded in a recording medium such as a compact disc read only memory (CD-ROM), a digital versatile disk read only memory (DVD-ROM), a magneto-optical (MO) disk, or a universal serial bus (USB) flash drive.

Moreover, in a case where the crystal analysis program disclosed in the present application is recorded in a recording medium as described above, the program may be directly used, or may be installed on a hard disk and then used through a recording medium reader included in a computer system, as needed. Furthermore, the crystal analysis program disclosed in the present application may be recorded in an external storage region (another computer or the like) accessible from the computer system through an information communication network. In this case, the crystal analysis program disclosed in the present application, which is recorded in the external storage region, can be used directly, or can be installed in a hard disk and then used from the external storage region through the information communication network, as needed.

Note that the crystal analysis program disclosed in the present application may be divided for every piece of any processing and recorded in a plurality of recording media.
(Computer-Readable Recording Medium)

A computer-readable recording medium disclosed in the present application records the crystal analysis program disclosed in the present application.

The computer-readable recording medium disclosed in the present application is not limited to any particular medium and can be appropriately selected depending on a purpose. Examples of the computer-readable recording medium include an internal hard disk, an external hard disk, a CD-ROM, a DVD-ROM, an MO disk, a USB memory, and the like, for example.

Furthermore, the computer-readable recording medium disclosed in the present application may be a plurality of recording media in which the crystal analysis program disclosed in the present application is divided and recorded for every piece of any processing.

Hereinafter, an example of the technology disclosed in the present application will be described in more detail using configuration examples of the device, flowcharts, and the like.

Figure 18:
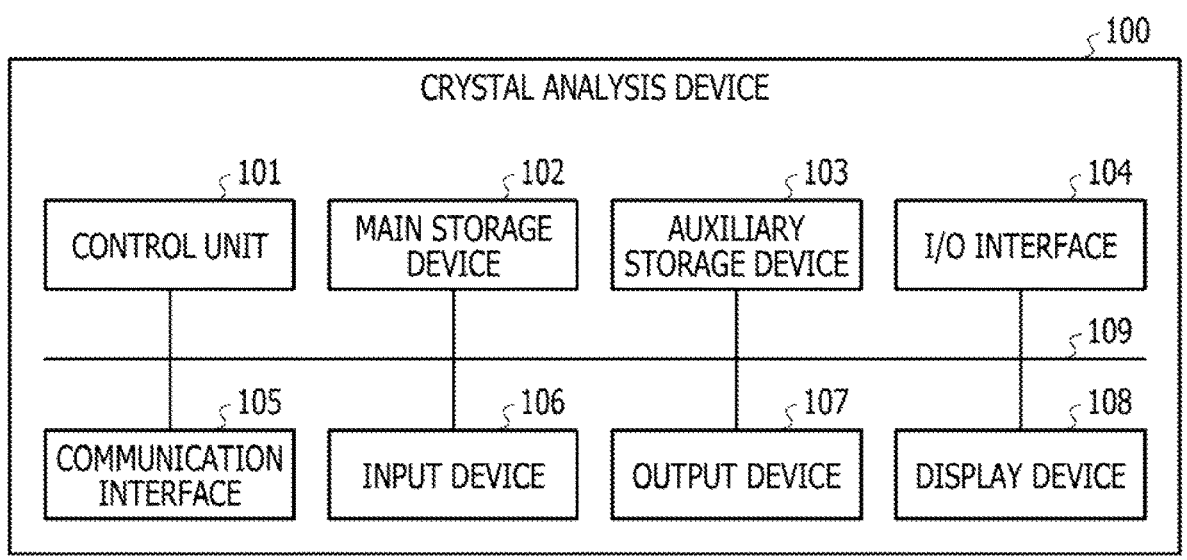
FIG. 18 is a diagram illustrating a hardware configuration example of a crystal analysis device disclosed in the present application.

FIG. 18 illustrates another hardware configuration example of the crystal analysis device disclosed in the present application.

In a crystal analysis device 100, for example, a control unit 101, a main storage device 102, an auxiliary storage device 103, an input/output (I/O) interface 104, a communication interface 105, an input device 106, an output device 107, and a display device 108 are connected to one another via a system bus 109.

The control unit 101 performs arithmetic operations (for example, four arithmetic operations, comparison operations, arithmetic operations for the annealing method, and the like), hardware and software operation control, and the like. The control unit 101 may be, for example, a central processing unit (CPU), a part of the annealing machine used for the annealing method, or a combination thereof.

The control unit 101 realizes various functions, for example, by executing a program (for example, the crystal analysis program disclosed in the present application or the like) read in the main storage device 102 or the like.

Processing performed by the graph creation unit and the analysis unit in the crystal analysis device disclosed in the present application can be performed by, for example, the control unit 101.

The main storage device 102 stores various programs and data or the like needed for executing various programs. As the main storage device 102, for example, a device having at least one of a read only memory (ROM) or a random access memory (RAM) can be used.

The ROM stores various programs, for example, a basic input/output system (BIOS) or the like. Furthermore, the ROM is not particularly limited, and can be appropriately selected depending on a purpose. Examples thereof include a mask ROM, a programmable ROM (PROM), and the like, for example.

The RAM functions, for example, as a work range expanded when various programs stored in the ROM, the auxiliary storage device 103, or the like are executed by the control unit 101. The RAM is not particularly limited, and can be appropriately selected depending on a purpose. Examples thereof include a dynamic random access memory (DRAM), a static random access memory (SRAM), and the like, for example.

The auxiliary storage device 103 is not particularly limited as long as the device can store various information and can be appropriately selected depending on a purpose. Examples thereof include a solid state drive (SSD), a hard disk drive (HDD), and the like, for example. Furthermore, the auxiliary storage device 103 may be a portable storage device such as a CD drive, a DVD drive, or a Blu-ray (registered trademark) disc (BD) drive.

Furthermore, the crystal analysis program disclosed in the present application is, for example, stored in the auxiliary storage device 103, loaded into the RAM (main memory) of the main storage device 102, and executed by the control unit 101.

The I/O interface 104 is an interface used to connect various external devices. The I/O interface 104 can input/output data to/from, for example, a compact disc ROM (CD-ROM), a digital versatile disk ROM (DVD-ROM), a magneto-optical disk (MO disk), a universal serial bus (USB) memory (USB flash drive), or the like.

The communication interface 105 is not particularly limited, and a known communication interface can be appropriately used. Examples thereof include a communication device using wireless or wired communication and the like, for example.

The input device 106 is not particularly limited as long as the device can receive input of various requests and information with respect to a crystal analysis device 100, and a known device can be appropriately used. Examples thereof include a keyboard, a mouse, a touch panel, a microphone, and the like, for example. Furthermore, in a case where the input device 106 is a touch panel (touch display), the input device 106 can also serve as the display device 108.

The output device 107 is not particularly limited, and a known device can be appropriately used. Examples thereof include a printer or the like, for example.

The display device 108 is not particularly limited, and a known device can be appropriately used. Examples thereof include a liquid crystal display, an organic EL display, and the like, for example FIG. 19 illustrates another hardware configuration example of the crystal analysis device disclosed in the present application.

Figure 19:
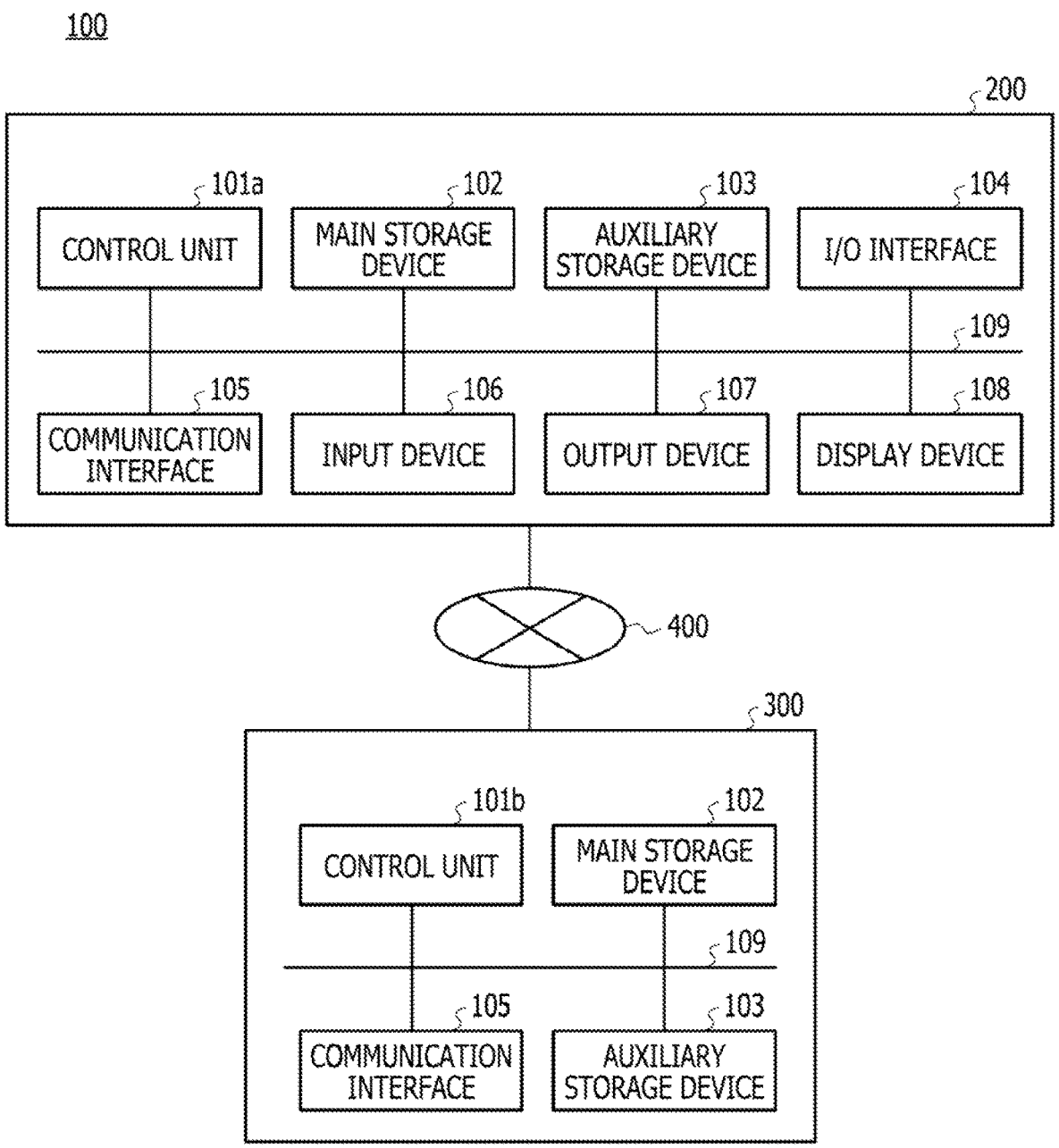
FIG. 19 is a diagram illustrating another hardware configuration example of the crystal analysis device disclosed in the present application.

In the example illustrated in FIG. 19, the crystal analysis device 100 is divided into a computer 200 that performs processing for creating a graph, analysis processing on a crystal, and the like, and an annealing machine 300 that performs optimization (ground state search) in the Ising model equation. Furthermore, in the example illustrated in FIG. 19, the computer 200 and the annealing machine 300 in the crystal analysis device 100 are connected via a network 400.

In the example illustrated in FIG. 19, for example, as a control unit 101a of the computer 200, a CPU or the like can be used, and as a control unit 101b of the annealing machine 300, a device specialized in the annealing method (annealing) can be used.

In the example illustrated in FIG. 19, for example, the computer 200 performs various settings for creating a graph, for analysis processing on a crystal, and for defining an Ising model equation. Then, information regarding values of a weight ($w_{ij}$) and a bias ($b_i$) in the Ising model equation is transmitted from the computer 200 to the annealing machine 300 via the network 400.

Next, the annealing machine 300 optimizes (minimize) the Ising model equation on the basis of the received information regarding the values of the weight ($w_{ij}$) and the bias ($b_i$) and obtains a minimum value of the Ising model equation and a state (state) of a bit that gives the minimum value. Then, the obtained minimum value of the Ising model equation and the obtained state (state) of the bit that gives the minimum value are transmitted from the annealing machine 300 to the computer 200 via the network 400.

Then, the computer 200 analyzes a crystal on the basis of the state (state) of the bit that gives the minimum value to the received Ising model equation.

Figure 20:
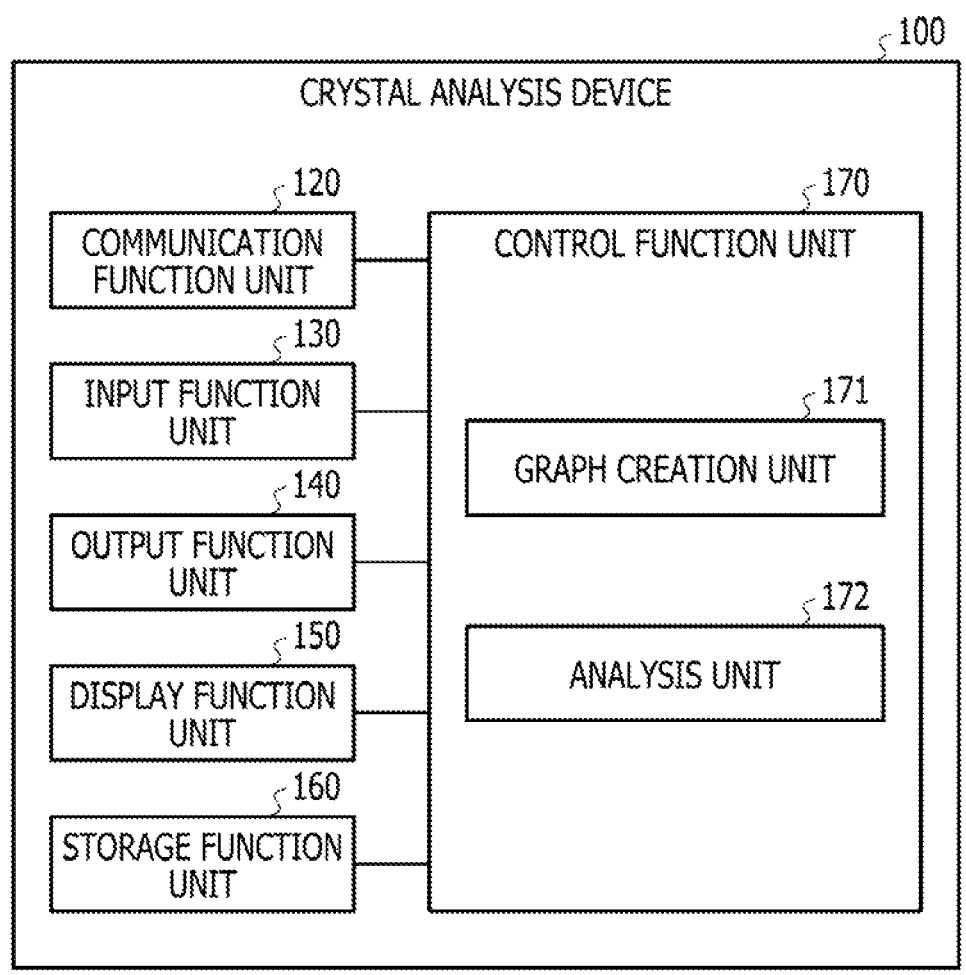
FIG. 20 is a diagram illustrating a functional configuration example of the crystal analysis device disclosed in the present application.

FIG. 20 illustrates an example of a functional configuration of the crystal analysis device disclosed in the present application.

As illustrated in FIG. 20, the crystal analysis device 100 includes a communication function unit 120, an input function unit 130, an output function unit 140, a display function unit 150, a storage function unit 160, and a control function unit 170.

The communication function unit 120, for example, transmits and receives various data to and from an external device. The communication function unit 120 may receive graph data, data regarding the bias and the weight in the Ising model equation, and the like from the external device, for example.

The input function unit 130 receives, for example, various instructions for the crystal analysis device 100. Furthermore, the input function unit 130 may receive, for example, graph data, an input of data regarding the bias and the weight in the Ising model equation, and the like.

The output function unit 140 prints and outputs, for example, crystal analysis result data and the like.

The display function unit 150 displays, for example, crystal analysis result data and the like on the display.

The storage function unit 160 stores, for example, various programs, graph data, data regarding the bias and the weight in the Ising model equation, and the like.

The control function unit 170 has a graph creation unit 171 and an analysis unit 172.

The graph creation unit 171 performs, for example, processing of creating a graph in which one repeating unit cell in a crystal is extended to an adjacent repeating unit cell adjacent to the one repeating unit cell, and the like. Moreover, the graph creation unit 171 performs, for example, processing of setting the number of intra-cell nodes that are data of an anionic atom to be n−1 or less, in an ionic crystal, when the number of intra-cell nodes that are data of the anionic atom bonded to a cationic atom in the one repeating unit cell is n.

The analysis unit 172 performs processing such as analysis of a crystal (ionic crystal) by using a graph created by the graph creation unit 171. More specifically, for example, the analysis unit 172 performs processing of, for example, computing a degree of similarity between the first crystal and the second crystal on the basis of, for example, the first graph and the second graph.

Figure 21:
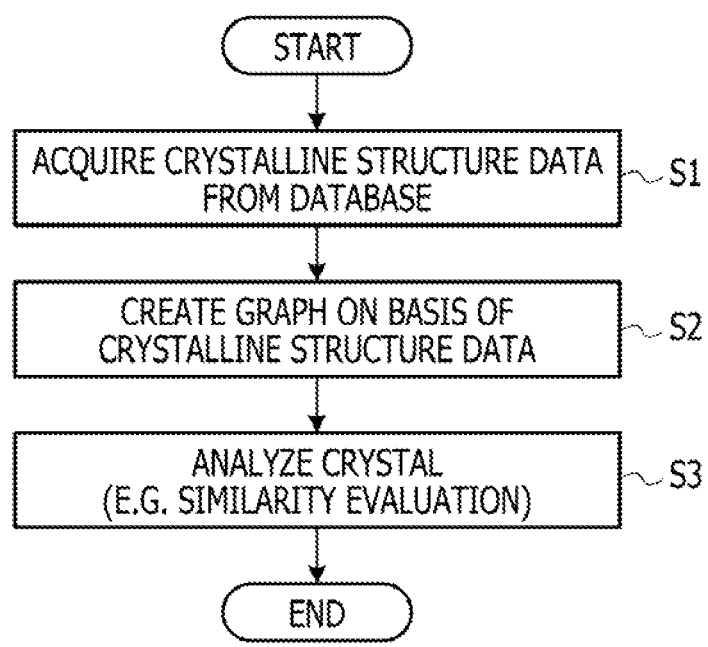
FIG. 21 is a diagram illustrating an example of a flowchart in analyzing an ionic crystal by using an example of the technology disclosed in the present application.

FIG. 21 illustrates an example of a flowchart in analyzing an ionic crystal by using an example of the technology disclosed in the present application.

First, the graph creation unit 171 acquires crystalline structure data from a database (S1). Here, the database from which the crystalline structure data is acquired is not particularly limited, and can be appropriately selected depending on a purpose. Examples thereof include an inorganic crystal structure database (ICSD) and the like, for example. Note that the number of pieces and the types of crystalline structure data to be acquired are not particularly limited, and can be appropriately selected depending on a purpose. For example, only crystalline structure data on chemicals having a specific element may be acquired.

Next, the graph creation unit 171 creates a graph on the basis of the acquired crystalline structure data (S2). Note that, details of a flow when creating the graph in S2 will be described later.

Then, the graph creation unit 171 analyzes a crystal by using the created graph (S3). Examples of crystal analysis include the computation of the degree of similarity described above, for example. The computation of the degree of similarity is performed by, for example, solving, with the annealing machine or the like, a maximum independent set problem in a conflict graph represented by an Ising model equation. The computation of the degree of similarity may be performed, for example, with reference to the following non-patent document.

Non-Patent Document: Maritza Hernandez, Arman Zaribafiyan, Maliheh Aramon, Mohammad Naghibi "A Novel Graph-based Approach for Determining Molecular Similarity". arXiv:1601.06693(https://arxiv.org/pdf/1601.06693.pdf)

Thus, it is possible to evaluate similarity in a crystalline structure, which is one of analyses of a crystalline structure.

FIGS. 22 to 26 illustrate an example of a flowchart in creating a graph by a technique of treating a repeating structure of a crystal as a loop structure, by using an example of the technology disclosed in the present application.

Figure 22:
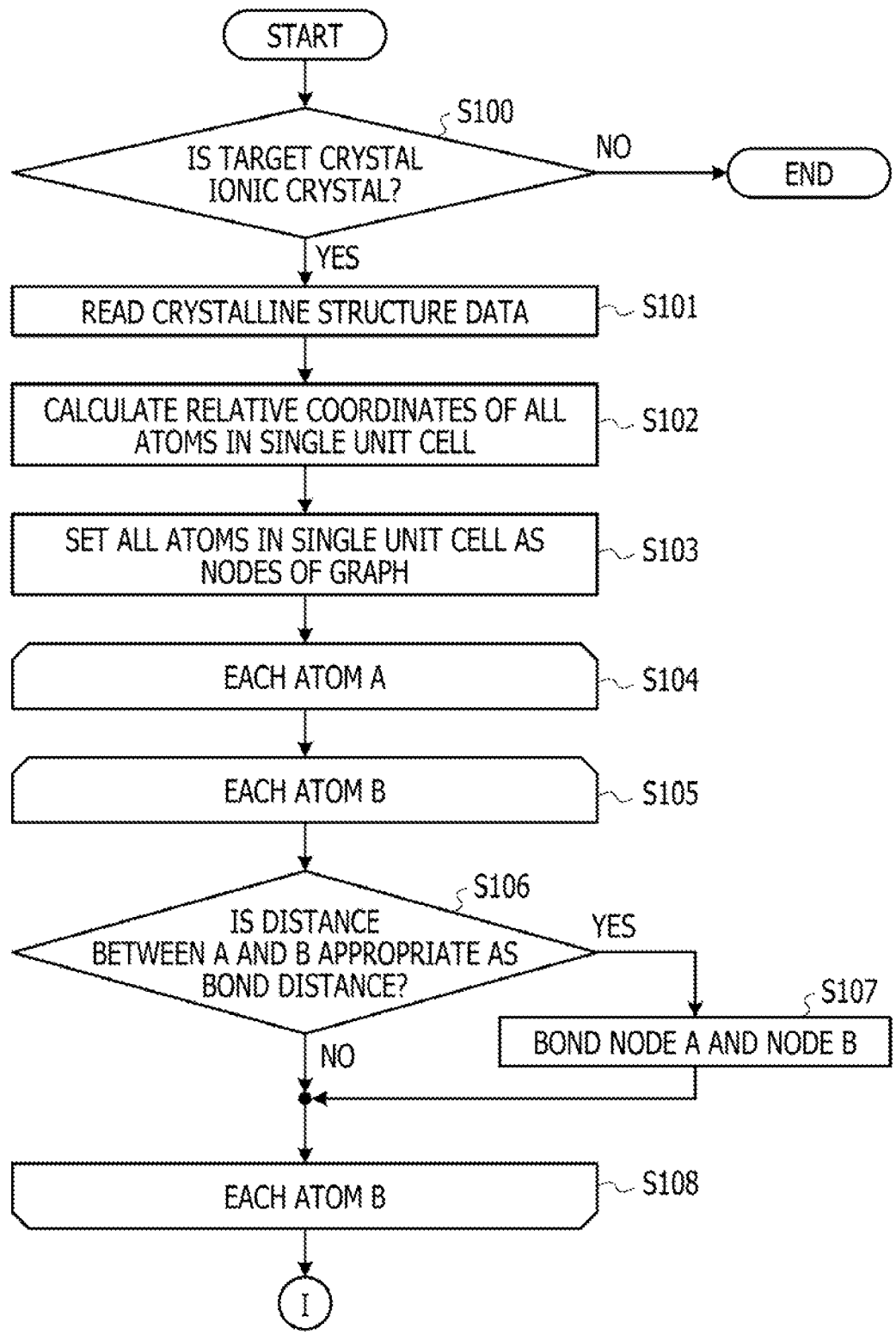
FIG. 22 is a diagram illustrating a part of an example of a flowchart in creating a graph by the technique of treating a repeating structure of a crystal as a loop structure, by using an example of the technology disclosed in the present application.

First, as illustrated in FIG. 22, the graph creation unit 171 determines whether or not a crystal to be analyzed is an ionic crystal (S100). In S100, in a case where the graph creation unit 171 determines that the crystal to be analyzed is an ionic crystal, the process is shifted to S101. In a case where the graph creation unit 171 determines that the crystal to be analyzed is not an ionic crystal, the process is ended.

Subsequently, the graph creation unit 171 reads crystalline structure data (S101).

Next, the graph creation unit 171 calculates relative coordinates of all the atoms in a single unit cell (S102). More specifically, for example, in S102, the graph creation unit 171 calculates relative coordinates of all the atoms in a single unit cell to obtain a relative positional relationship of all atoms.

Then, the graph creation unit 171 sets all the atoms in the single unit cell as nodes of a graph (S103). Furthermore, the node prepared in S103 is an intra-cell node in a repeating unit cell.

Here, S104 and S116 mean that the processes S105 to S115 described later are performed (repeated) for all the atoms corresponding to a certain atom A in the single unit cell. Likewise, S105 and S108 mean that the processes of S106 and S107 described later are performed (repeated) for all combinations of a certain atom (atom A) and another atom B.

Furthermore, for a combination of two atoms (A and B), that is, for example, a certain atom (atom A) and another atom (atom B) other than the certain atom among all the atoms in the single unit cell, the graph creation unit 171 determines whether a distance between A and B is appropriate as a bond distance (S106). Then, if the distance between A and B is appropriate as a bond distance, the graph creation unit 171 bonds a node A and a node B (S107). In other words, for example, in S107, the graph creation unit 171 provides an edge corresponding to between the node A and the node B. Furthermore, the edge provided in S107 is an intra-cell edge in a repeating unit cell.

Furthermore, if the distance between A and B is not appropriate as a bond distance, the graph creation unit 171 shifts the process to S108.

Figure 23:
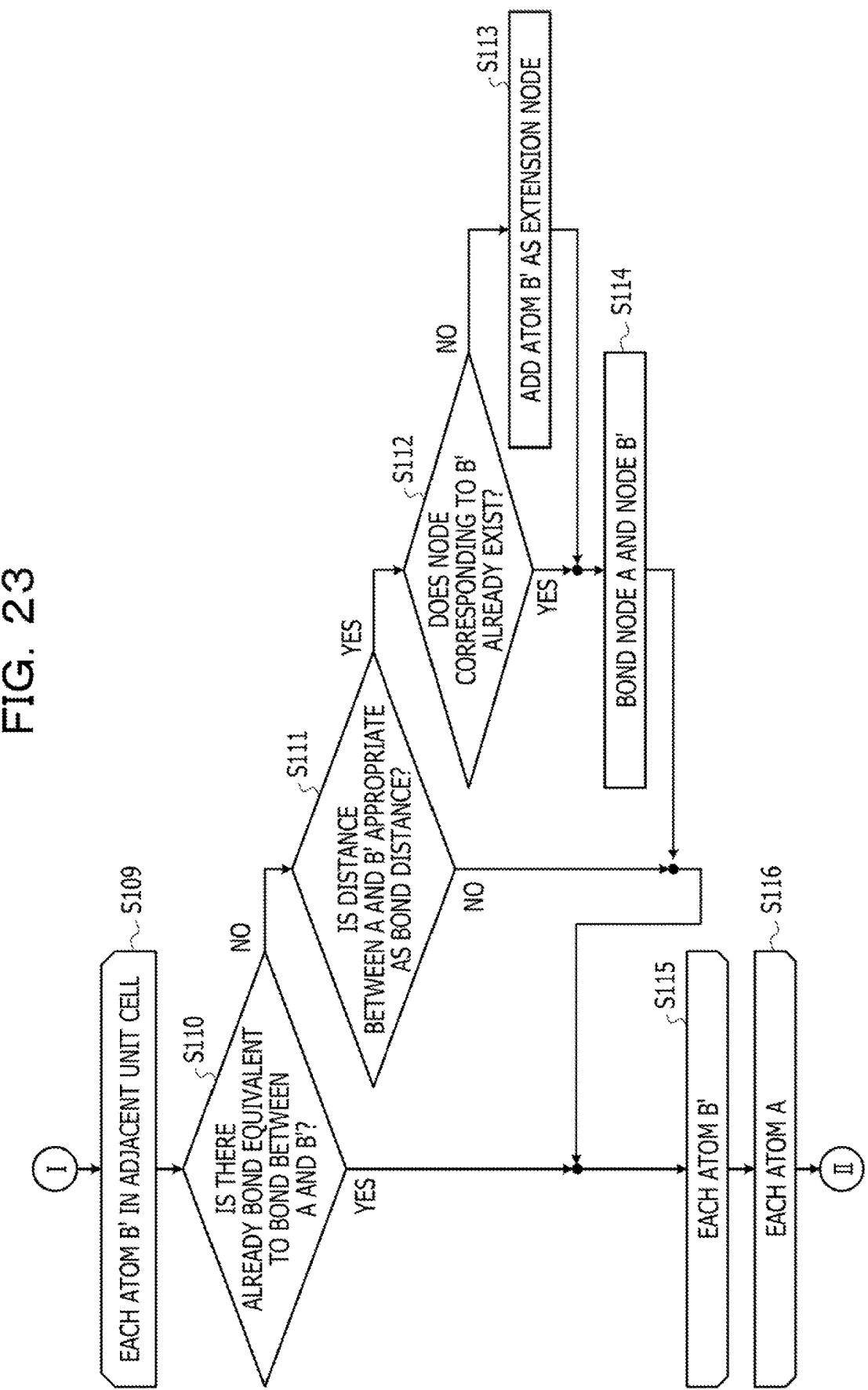
FIG. 23 is a diagram illustrating a part of the example of the flowchart in creating a graph by the technique of treating a repeating structure of a crystal as a loop structure, by using an example of the technology disclosed in the present application.

Subsequently, in FIGS. 23, S109 and S115 mean that the processes of S110 and S114 described later are performed (repeated) for all combinations of a certain atom (atom A) and another atom B'.

Then, the graph creation unit 171 determines whether there is already a bond equivalent to a bond between A and B', between the certain atom (atom A) in the single unit cell and any atom B' in an adjacent unit cell (S110). If there is no bond equivalent to the bond between A and B' yet in S110, the graph creation unit 171 determines whether a distance between A and B' is appropriate as a bond distance (S111).

Moreover, if the distance between A and B' is appropriate as a bond distance, the graph creation unit 171 determines whether a node corresponding to B' already exists (S112). Thereafter, if it is determined that there is no node corresponding to B', the graph creation unit 171 adds the atom B' as an extension node (S113). Next, after adding the atom B' as an extension node, the graph creation unit 171 bonds the node A and the node B'(S114). In other words, for example, in S114, the graph creation unit 171 provides an edge corresponding to between the node A and the node B'.

Furthermore, if the graph creation unit 171 determines in S112 that the node corresponding to B' already exists, the graph creation unit 171 shifts the process to S114 and bonds the node A and the node B'.

Here, in any case of when it is determined in S110 that there is no bond equivalent to the bond between A and B', when it is determined in S111 that the distance between A and B' is not appropriate as a bond distance, and when the process of S114 is performed, the graph creation unit 171 shifts the process to S115 such that the processes from S110 to S114 are performed (repeated) for all combinations of a certain atom (atom A) and another atom B'.

Figure 24:
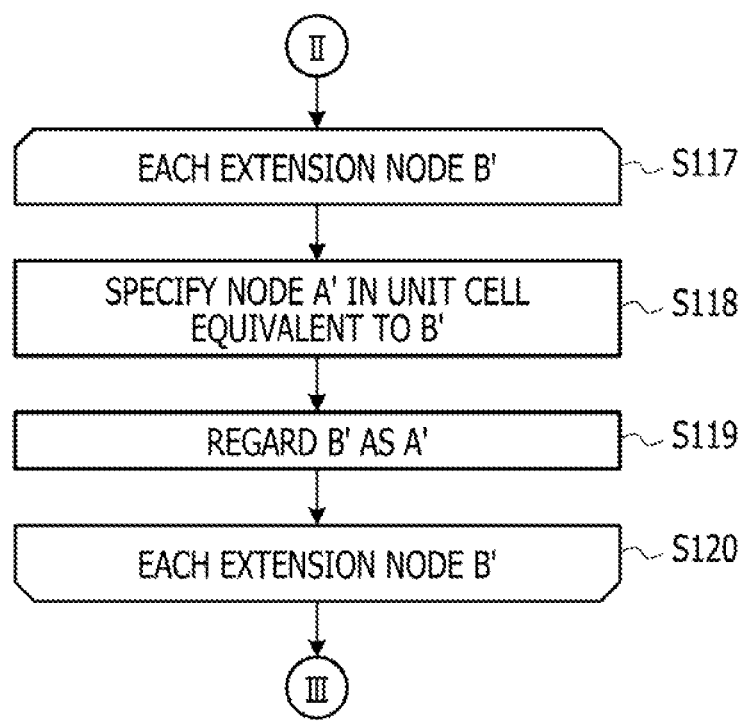
FIG. 24 is a diagram illustrating a part of the example of the flowchart in creating a graph by the technique of treating a repeating structure of a crystal as a loop structure, by using an example of the technology disclosed in the present application.

Subsequently, in FIGS. 24, S117 and S120 mean that the processes of S118 and S119 described later are performed (repeated) in all the extension nodes.

Then, the graph creation unit 171 specifies a node A' in a unit cell equivalent to the extension node B' (S118).

Next, the graph creation unit 171 regards the extension node B' as node A'(S119). That is, for example, in S119, by regarding the extension node B' as the node A', the graph creation unit 171 sets an edge corresponding to between the node A and the node A' as a loop edge.

Figure 25:
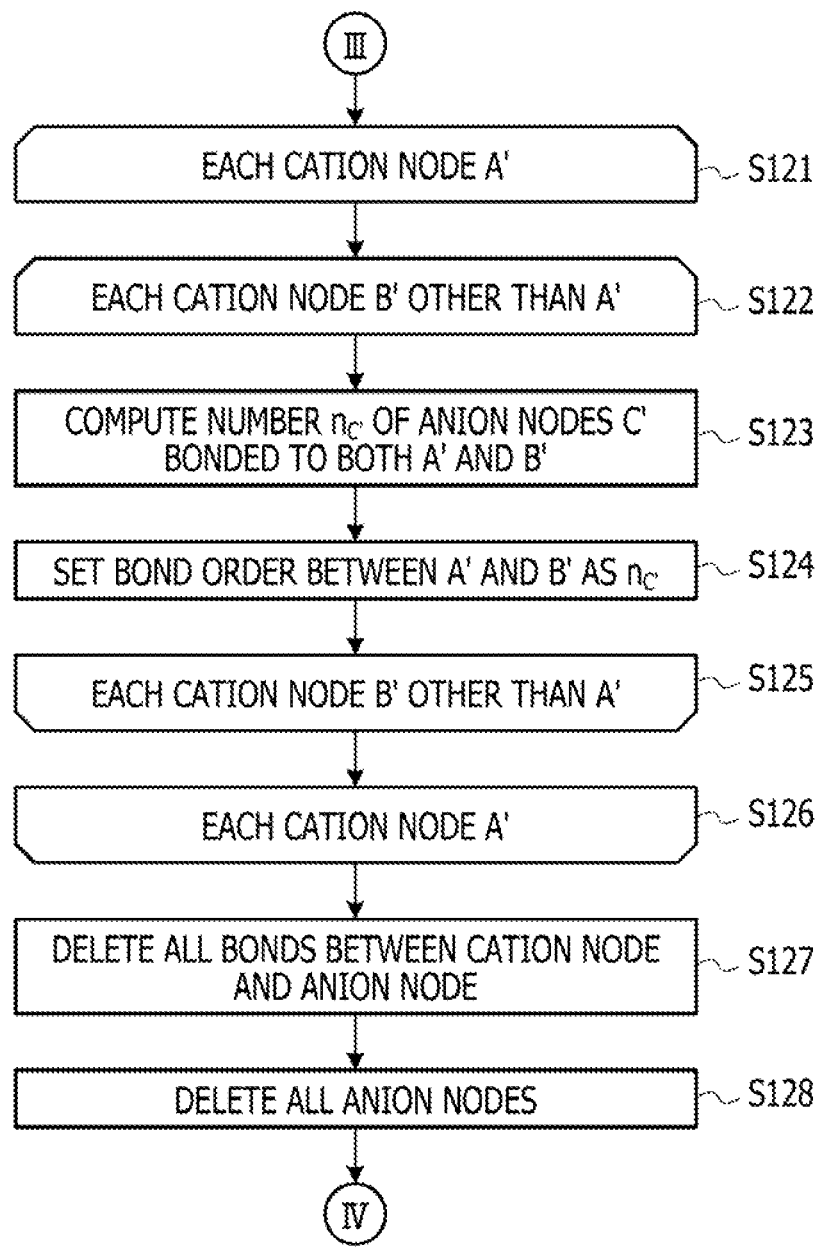
FIG. 25 is a diagram illustrating a part of the example of the flowchart in creating a graph by the technique of treating a repeating structure of a crystal as a loop structure, by using an example of the technology disclosed in the present application.

Then, in FIGS. 25, S121 and S126 mean that the processes of S122 to S125 described later are performed (repeated) in all the individual cation nodes A'. Likewise, S122 and S125 mean that the processes of S123 and S124 described later are performed (repeated) in all the individual cation nodes B' other than the cation nodes A'.

The graph creation unit 171 computes $n_{C'}$, which is the number of anion nodes (cationic atom nodes) C' bonded to both the cation node (cationic atom node) A' and the cation node B'. (S123).

Next, the graph creation unit 171 sets a bond order between the cation node A' and the cation node B' as $n_{C'}$ (S124). That is, for example, in S124, the graph creation unit 171 specifies a bond order between the cation node A' and the cation node B' on the basis of the number of anion nodes C'.

Subsequently, the graph creation unit 171 deletes all the bonds (edges) between the cation node and the anion node (S127). Moreover, the graph creation unit 171 deletes all the anion nodes (S128). That is, for example, in S128, the graph creation unit 171 sets the number of intra-cell nodes that are data of an anionic atom to 0.

By doing so, in the examples illustrated in FIGS. 22 to 26, the number of nodes contained in the repeating unit cell can be reduced, and the number of bits required for the analysis of the ionic crystal can be further suppressed.

Figure 26:
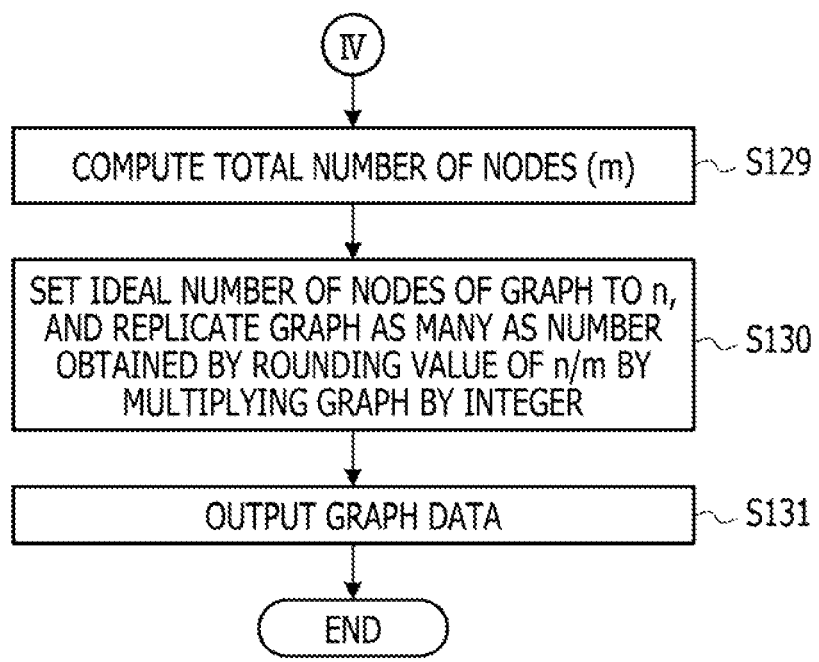
FIG. 26 is a diagram illustrating a part of the example of the flowchart in creating a graph by the technique of treating a repeating structure of a crystal as a loop structure, by using an example of the technology disclosed in the present application.

Next, in FIG. 26, the graph creation unit 171 computes a total number of nodes (m) (S129). That is, for example, in S129, the graph creation unit 171 counts the number of cation nodes in the unit cell and specifies the total number of nodes (m).

Next, the graph creation unit 171 sets an ideal number of nodes of the graph to n, computes a value of n/m, then specifies a number obtained by rounding the value of n/m, and replicates the graph as many as the specified number by multiplying the graph by an integer (S130). That is, for example, in S130, the graph creation unit 171 multiplies the graph by an integer so as to approach the ideal number of nodes n of the graph. Note that the ideal number of nodes n of the graph can be appropriately selected in accordance with the target ionic crystal.

Subsequently, the graph creation unit 171 outputs the graph data (S131).

Then, when the output of the graph data is completed, the graph creation unit 171 ends the process of creating the graph.

Figure 27:
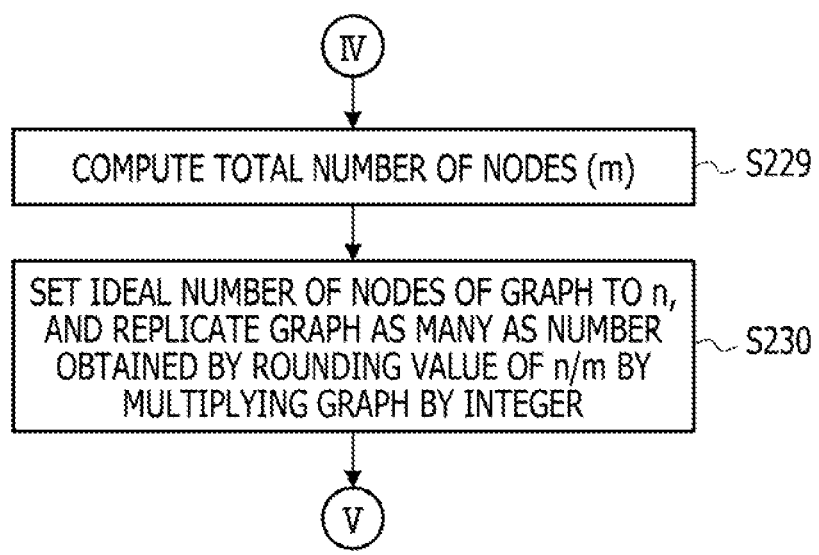
FIG. 27 is a diagram illustrating a part of an example of a flowchart in creating a graph by the technique of extending and handling a unit cell by using an extension node, by using an example of the technology disclosed in the present application.
Figure 28:
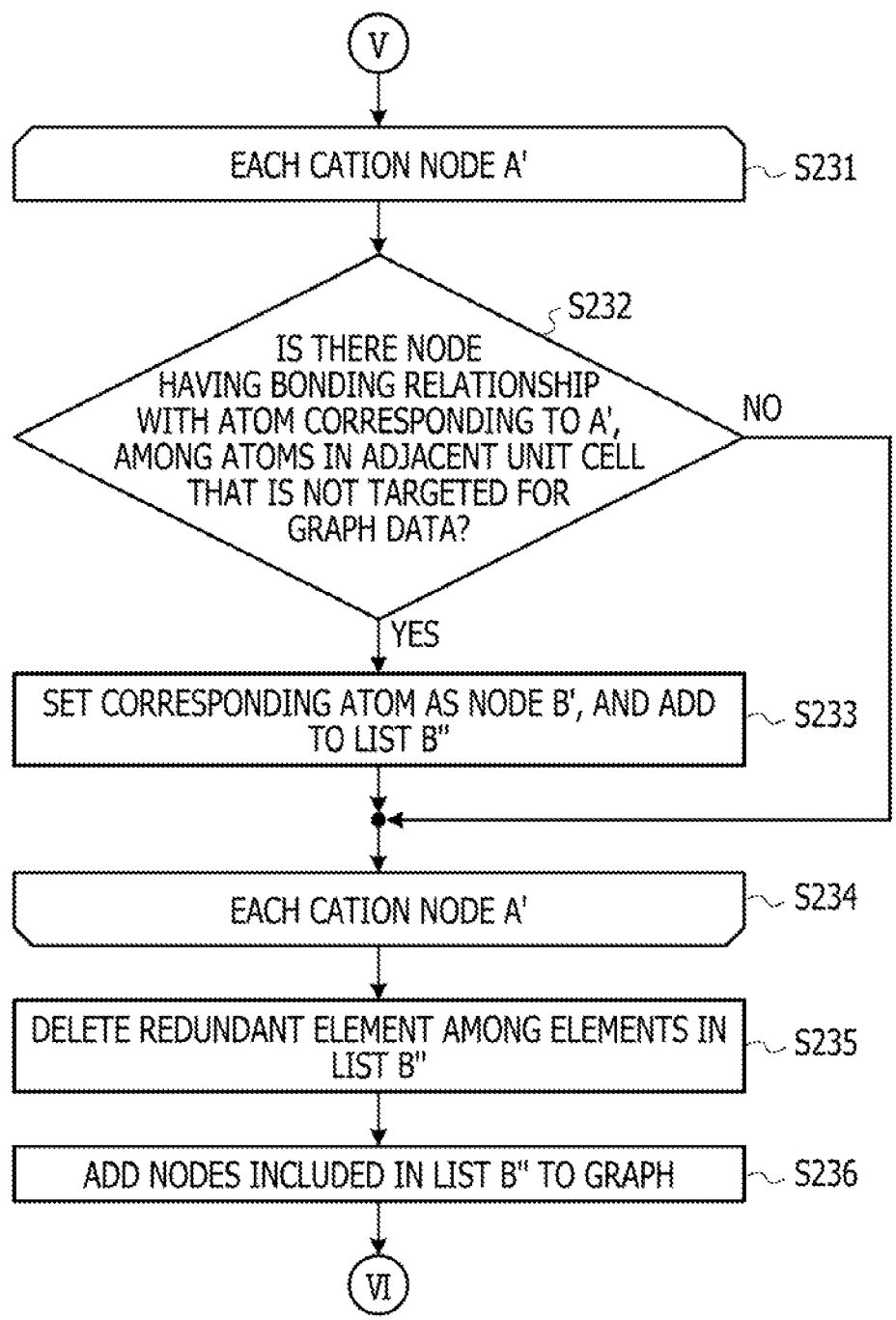
FIG. 28 is a diagram illustrating a part of the example of the flowchart in creating a graph by the technique of extending and handling a unit cell by using an extension node, by using an example of the technology disclosed in the present application.
Figure 29:
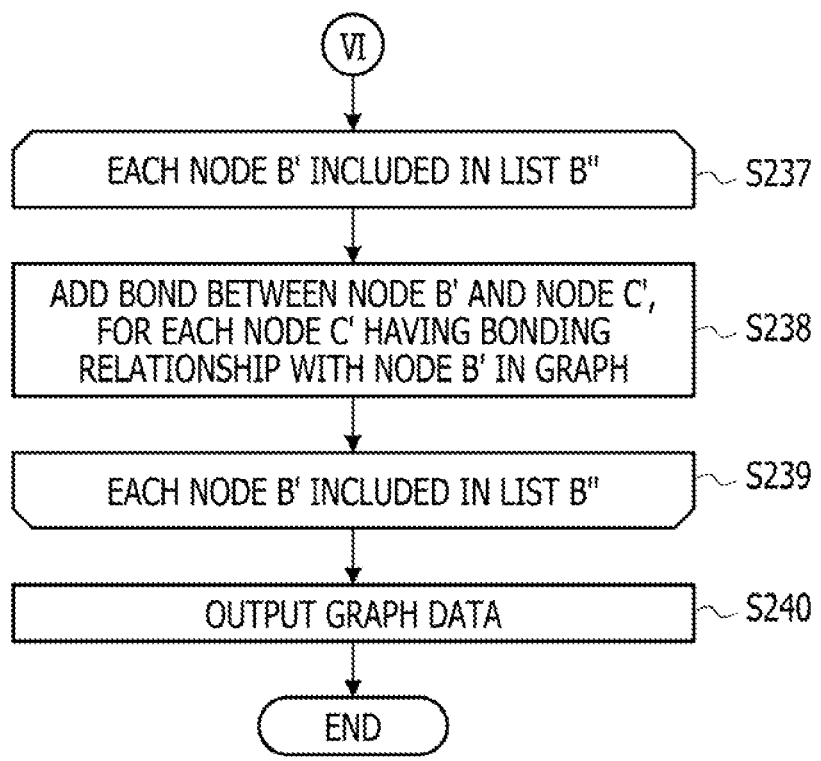
FIG. 29 is a diagram illustrating a part of the example of the flowchart in creating a graph by the technique of extending and handling a unit cell by using an extension node, by using an example of the technology disclosed in the present application.

FIGS. 27 to 29 illustrate an example of a flowchart in creating a graph by a technique of extending and handling a unit cell by using an extension node, by using an example of the technology disclosed in the present application.

Note that, in the technique of extending and handling a unit cell by using an extension node, similar processes can be performed for S100 to S128 in the flows described in FIGS. 22 to 26, and thus the description thereof will be omitted.

In the technique of extending a unit cell by using an extension node, as illustrated in FIG. 27, the graph creation unit 171 computes a total number of nodes (m) similarly to S129 in FIG. 26 (S229). Next, that is, for example, in S129, the graph creation unit 171 counts the number of cation nodes in the unit cell and specifies the total number of nodes (m).

Next, as illustrated in FIG. 27, similarly to S130 in FIG. 26, the graph creation unit 171 sets n to an ideal number of nodes of the graph, computes a value of n/m, then specifies a number obtained by rounding the value of n/m, and replicates the graph as many as the specified number by multiplying the graph by an integer (S230).

In FIGS. 28, S231 and S234 mean that the processes of S232 and S233 described later are performed (repeated) in all the individual cation nodes A'.

The graph creation unit 171 determines whether or not there is a node having a bonding relationship with an atom corresponding to A', among atoms in an adjacent unit cell that are not targeted for the graph (S232). In S232, if the graph creation unit 171 determines that there is a node having a bonding relationship with an atom corresponding to A', the process is shifted to S233. If the graph creation unit 171 determines that there is no node having a bonding relationship with an atom corresponding to A', the process is shifted to S234.

Next, the graph creation unit 171 sets, as the node B', the atom determined in S232 to be a node having a bonding relationship with the atom corresponding to A', and adds to a list B".

Subsequently, the graph creation unit 171 deletes a redundant element among elements (nodes) in the list B" (S235). Next, the graph creation unit 171 adds nodes included in the list B" to the graph (S236).

In FIGS. 29, S237 and S239 mean that the process of S238 described later is performed (repeated) in all the individual nodes B' included in the list B".

The graph creation unit 171 adds a bond (edge) between the node B' and a node C' for each node C having a bonding relationship with the node B' in the graph (S238).

Subsequently, the graph creation unit 171 outputs the graph data (S240).

Then, when the output of the graph data is completed, the graph creation unit 171 ends the process of creating the graph.

Furthermore, in FIGS. 21 to 29, the flow of the processing in an example of the technology disclosed in the present application has been described according to a specific order. However, in the technology disclosed in the present application, it is possible to appropriately switch an order of individual steps in a technically possible range. Furthermore, in the technology disclosed in the present application, a plurality of steps may be collectively performed in a technically possible range.

Examples of the annealing method and the annealing machine will be described below.

The annealing method is a method for probabilistically working out a solution using superposition of random number values and quantum bits. The following describes a problem of minimizing a value of an evaluation function to be optimized as an example. The value of the evaluation function is referred to as energy. Furthermore, in a case where the value of the evaluation function is maximized, the sign of the evaluation function only needs to be changed.

First, a process is started from an initial state in which one of discrete values is assigned to each variable. With respect to a current state (combination of variable values), a state close to the current state (for example, a state in which only one variable is changed) is selected, and a state transition therebetween is considered. An energy change with respect to the state transition is calculated. Depending on the value, it is probabilistically determined whether to adopt the state transition to change the state or not to adopt the state transition to keep the original state. In a case where an adoption probability when the energy goes down is selected to be larger than that when the energy goes up, it can be expected that a state change will occur in a direction that the energy goes down on average, and that a state transition will occur to a more appropriate state over time. Therefore, there is a possibility that an optimum solution or an approximate solution that gives energy close to the optimum value can be obtained finally.

If this is adopted when the energy goes down deterministically and is not adopted when the energy goes up, the energy change decreases monotonically in a broad sense with respect to time, but no further change occurs when reaching a local solution. As described above, since there are a very large number of local solutions in the discrete optimization problem, a state is almost certainly caught in a local solution that is not so close to an optimum value. Therefore, when the discrete optimization problem is solved, it is important to determine probabilistically whether to adopt the state.

In the annealing method, it has been proved that, by determining an adoption (permissible) probability of a state transition as follows, a state reaches an optimum solution in the limit of infinite time (iteration count).

Hereinafter, a method for working out an optimum solution using the annealing method will be described step by step.

(1) For an energy change (energy reduction) value ($-\Delta E$) due to a state transition, a permissible probability p of the state transition is determined by any one of the following functions f( ).

[Formula 9]
$$p(\Delta E, T) = f(-\Delta E/T) \quad \text{(EQUATION 1-1)}$$

[Formula 10]
$$f_{metro}(x) = \min(1, e^x) \quad \text{(METROPOLIS METHOD) (EQUATION 1-2)}$$

[Formula 11]
$$f_{Gibbs}(x) = \frac{1}{1+e^{-x}} \quad \text{(GIBBS METHOD) (EQUATION 1-3)}$$

Here, T represents a parameter called a temperature value and can be changed as follows, for example.

(2) The temperature value T is logarithmically reduced with respect to an iteration count t as represented by the following equation.

[Formula 12]
$$T = \frac{T_0 \log(c)}{\log(t+c)} \quad \text{(EQUATION 2)}$$

Here, $T_0$ is an initial temperature value, and is desirably a sufficiently large value depending on a problem.

In a case where the permissible probability represented by the equation in (1) is used, if a steady state is reached after sufficient iterations, an occupation probability of each state follows a Boltzmann distribution for a thermal equilibrium state in thermodynamics.

Then, when the temperature is gradually lowered from a high temperature, an occupation probability of a low energy state increases. Therefore, it is considered that the low energy state is obtained when the temperature is sufficiently lowered. Since this state is very similar to a state change caused when a material is annealed, this method is referred to as the annealing method (or pseudo-annealing method).

Note that probabilistic occurrence of a state transition that increases energy corresponds to thermal excitation in the physics.

Figure 30:
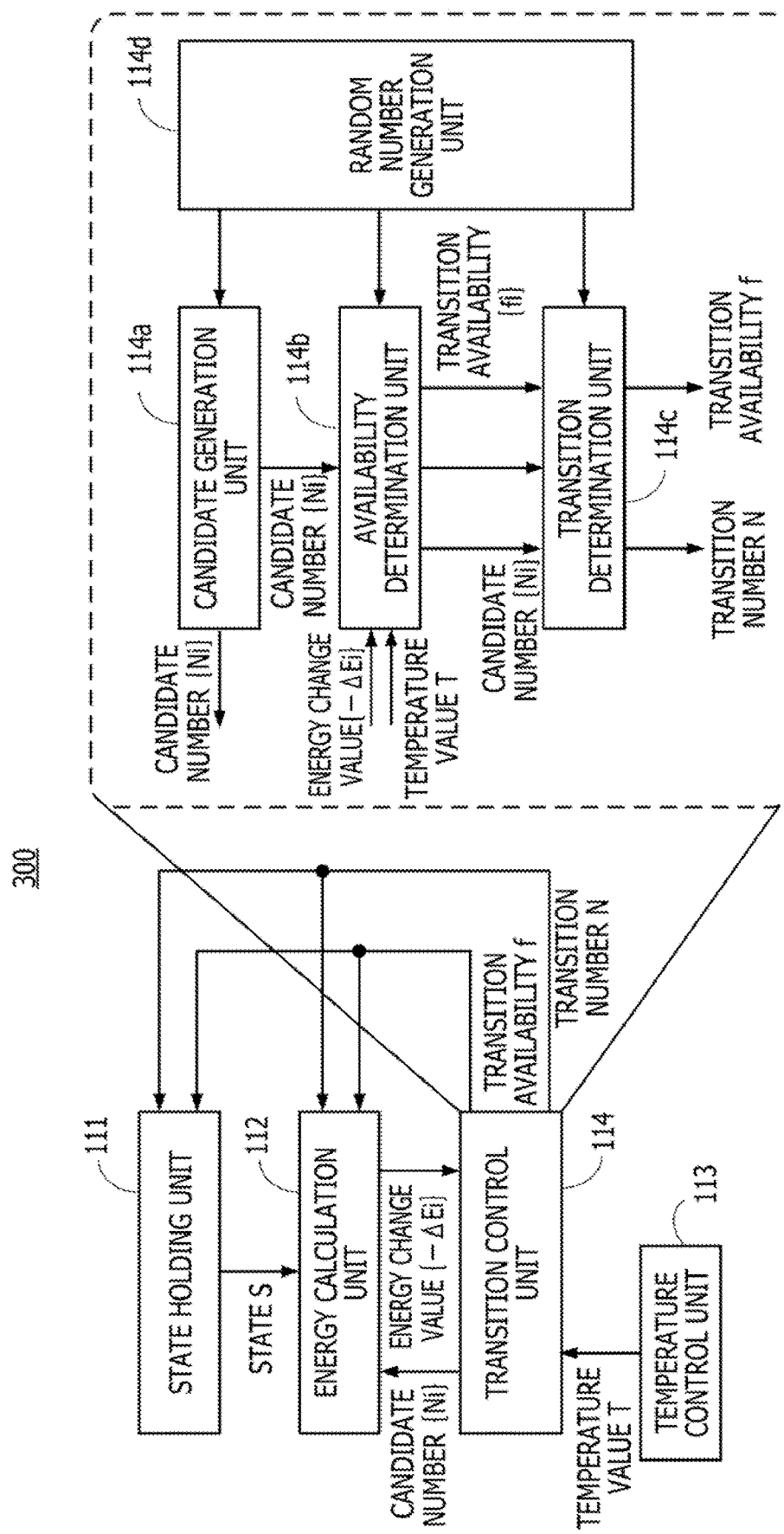
FIG. 30 is a diagram illustrating an example of a functional configuration of an annealing machine that performs an annealing method.

FIG. 30 illustrates an example of a functional configuration of an annealing machine that performs the annealing method. However, in the following description, a case of generating a plurality of state transition candidates is also described, but a basic annealing method generates one transition candidate at a time.

The annealing machine 300 includes a state holding unit 111 that holds a current state S (a plurality of state variable values). Furthermore, the annealing machine 300 includes an energy calculation unit 112 that calculates an energy change value $\{-\Delta Ei\}$ of each state transition when a state transition from the current state S occurs due to a change in any one of the plurality of state variable values. Moreover, the annealing machine 300 includes a temperature control unit 113 that controls the temperature value T, and a transition control unit 114 that controls a state change. Note that the annealing machine 300 can be a part of the above-described crystal analysis device 100.

The transition control unit 114 probabilistically determines whether or not to accept any one of a plurality of state transitions according to a relative relationship between the energy change value $\{-\Delta Ei\}$ and thermal excitation energy, based on the temperature value T, the energy change value $\{-\Delta Ei\}$, and a random number value.

Here, the transition control unit 114 includes a candidate generation unit 114a that generates a state transition candidate, and an availability determination unit 114b to probabilistically determine whether or not to permit a state transition for each candidate based on the energy change value $\{-\Delta Ei\}$ and the temperature value T. Moreover, the transition control unit 114 includes a transition determination unit 114c that determines a candidate to be adopted from the candidates that have been permitted, and a random number generation unit 114d that generates a random variable.

The operation of the annealing machine 300 in one iteration is as follows.

First, the candidate generation unit 114a generates one or more state transition candidates (candidate number {Ni}) from the current state S held in the state holding unit 111 to a next state. Next, the energy calculation unit 112 calculates the energy change value $\{-\Delta Ei\}$ for each state transition listed as a candidate by using the current state S and the state transition candidates. The availability determination unit 114b permits a state transition with a permissible probability of the above Equation (1) according to the energy change value $\{-\Delta Ei\}$ of each state transition using the temperature value T generated by the temperature control unit 113 and the random variable (random number value) generated by the random number generation unit 114d.

Then, the availability determination unit 114b outputs availability {fi} of each state transition. In a case where there is a plurality of permitted state transitions, the transition determination unit 114c randomly selects one of the permitted state transitions using a random number value. Then, the transition determination unit 114c outputs a transition number N and transition availability f of the selected state transition. In a case where there is a permitted state transition, a state variable value stored in the state holding unit 111 is updated according to the adopted state transition.

Starting from an initial state, the above-described iteration is repeated while the temperature value is lowered by the temperature control unit 113. When a completion determination condition such as reaching a certain iteration count or energy falling below a certain value is satisfied, the operation is completed. An answer output by the annealing machine 300 is a state when the operation is completed.

The annealing machine 300 illustrated in FIG. 30 may be implemented by using, for example, a semiconductor integrated circuit. For example, the transition control unit 114 may include a random number generation circuit that functions as the random number generation unit 114d, a comparison circuit that functions as at least a part of the availability determination unit 114b, a noise table to be described later, or the like.

Regarding the transition control unit 114 illustrated in FIG. 30, details of a mechanism that permits a state transition at a permissible probability represented in the Equation (1) will be further described.

A circuit that outputs 1 at the permissible probability p and outputs 0 at a permissible probability (1−p) can be achieved by inputting the permissible probability p for input A and a uniform random number that takes a value of a section [0, 1) for input B in a comparator that has the two inputs A and B, and outputs 1 when A>B is satisfied and outputs 0 when A<B is satisfied. Therefore, if the value of the permissible probability p calculated based on the energy change value and the temperature value T using the equation in (1) is input to input A of this comparator, the above-described function can be achieved.

In other words, for example, with a circuit that outputs 1 when f(ΔE/T) is larger than u, in which f is a function used in the equation in (1), and u is a uniform random number that takes a value of the section [0, 1), the above-described function can be achieved.

Furthermore, the same function as the above-described function can also be achieved by making the following modification.

Applying the same monotonically increasing function to two numbers does not change a magnitude relationship. Therefore, an output is not changed even if the same monotonically increasing function is applied to two inputs of the comparator. If an inverse function $f^{-1}$ of f is adopted as this monotonically increasing function, it can be seen that a circuit that outputs 1 when −ΔE/T is larger than $f^{-1}(u)$ can be adopted. Moreover, since the temperature value T is positive, it can be seen that a circuit that outputs 1 when −ΔE is larger than $Tf^{-1}(u)$ may be adopted.

The transition control unit 114 in FIG. 30 may include a noise table that is a conversion table that realizes the inverse function $f^{-1}(u)$, and outputs a value of a next function with respect to an input that is a discretized section [0, 1).

[Formula 13]

$$F_{metro}^{-1}(u) = \log(u) \qquad \text{(EQUATION 3-1)}$$

[Formula 14]

$$f_{Gibbs}^{-1}(u) = \log\left(\frac{u}{1-u}\right) \qquad \text{(EQUATION 3-2)}$$

Figure 31:
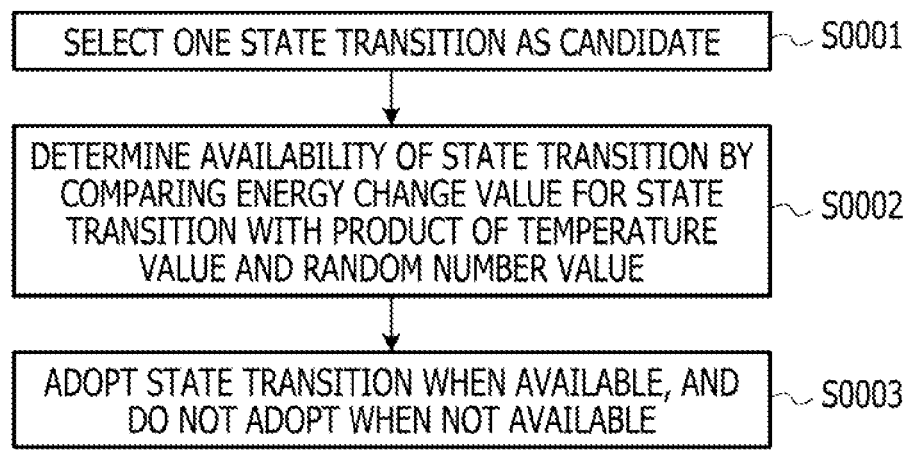
FIG. 31 is a diagram illustrating an example of an operation flow of a transition control unit 114.

FIG. 31 is a diagram illustrating an example of an operation flow of the transition control unit 114. The operation flow illustrated in FIG. 31 includes a step of selecting one state transition as a candidate (S0001), a step of determining availability of the state transition by comparing an energy change value for the state transition with a product of a temperature value and a random number value (S0002), and a step of adopting the state transition when the state transition is available, and not adopting the state transition when the state transition is not available (S0003).

EXAMPLES

Examples of the technology disclosed in the present application will be described. However, the technology disclosed in the present application is not limited to the examples.

Example 1

As Example 1, a degree of similarity in an ionic crystal was computed using an example of the crystal analysis device disclosed in the present application.

The degree of similarity of the ionic crystals in Example 1 was computed by using a crystal analysis device having a hardware configuration as illustrated in FIG. 19 in accordance with the flowcharts of FIGS. 21 to 26. Note that, in Example 1, a graph was created without performing S129 and S130 in FIG. 26 (without multiplying the graph by an integer), and the degree of similarity was calculated.

More specifically, for example, in Example 1, the graph is extended using a technique of treating a repeating structure of the ionic crystal as a loop structure, and the following Equation (1) was minimized by an annealing method by using Digital Annealer (registered trademark) as an annealing machine.

[Formula 15]

$$E = -\alpha \sum_i x_i + \beta \sum_i \sum_j c'_{i,j} x_i x_j \quad \text{EQUATION (1)}$$

Here, in Equation (1),

E is a Hamiltonian in which minimizing E means searching for a maximum independent set, $c'_{ij}$ is a coefficient representing a weight regarding a bond order between an i-th node and the j-th node in a conflict graph between a first graph and a second graph, $x_i$ is a binary variable representing that the i-th node has 0 or 1, $x_j$ is a binary variable representing that the j-th node has 0 or 1, and $\alpha$ and $\beta$ are positive numbers.

Moreover, in Example 1, the degree of similarity was computed by using the following Equation (2), for the obtained maximum independent set.

[Formula 16]

$$S(G_A, G_B) = \delta \max\left\{ \frac{|V_C^A|}{|V_A|}, \frac{|V_C^B|}{|V_B|} \right\} + (1-\delta)\min\left\{ \frac{|V_C^A|}{|V_A|}, \frac{|V_C^B|}{|V_B|} \right\} \quad \text{EQUATION (2)}$$

In the above Equation (2), $S(G_A, G_B)$ represents a degree of similarity between a first crystal represented as the first graph and a second crystal represented as the second graph, is represented by 0 to 1, and means a higher degree of similarity as approaching to 1, $V_A$ represents a total number of node atoms in the first crystal represented as the first graph, $V_C^A$ represents the number of node atoms included in the maximum independent set of the conflict graph among node atoms in the first crystal represented as the first graph, and $V_B$ represents a total number of node atoms in the second crystal represented as the second graph, $V_C^B$ represents the number of node atoms included in the maximum independent set of the conflict graph among node atoms in the second crystal represented as the second graph, and $\delta$ is a number from 0 to 1.

Here, in Example 1, the degree of similarity was computed for an ionic crystal A in which the number of atoms contained in a repeating unit cell is 76 and an ionic crystal B in which the number of atoms contained in a repeating unit cell is 96. Note that a structure of the repeating unit cell of the ionic crystal A is the one illustrated in FIG. 15A described above, and a structure of the repeating unit cell of the ionic crystal B is the one illustrated in FIG. 15B described above.

Here, as illustrated in FIG. 15A, the ionic crystal A has eight pieces of lithium (Li), four pieces of manganese (Mn), 16 pieces of phosphorus (P), and 48 pieces of oxygen (O) individually in the unit cell, and has a total of 76 atoms. Likewise, as illustrated in FIG. 15B, the ionic crystal B has 16 pieces of lithium (Li), eight pieces of manganese (Mn), 16 pieces of phosphorus (P), and 56 pieces of oxygen (O) individually in the unit cell, and has a total of 96 atoms.

Note that the ionic crystal A is a crystal of "ICSD #253225" whose composition formula is represented by "$Li_2MnP_2O_7$", while the ionic crystal B is a crystal of "ICSD #248405" whose composition formula is represented by "$Li_2Mn(PO_3)_4$".

In Example 1, a conflict graph was created after deleting nodes of 48 oxygen atoms contained in the repeating unit cell of the ionic crystal A and nodes of 56 oxygen atoms contained in the repeating unit cell of the ionic crystal B. That is, for example, in Example 1, the number of nodes was set to 28 by deleting the nodes of 48 oxygen atoms from the ionic crystal A having 76 nodes, and the number of nodes was set to 40 by deleting the nodes of 56 oxygen atoms from the ionic crystal B having 96 nodes.

Figure 32:
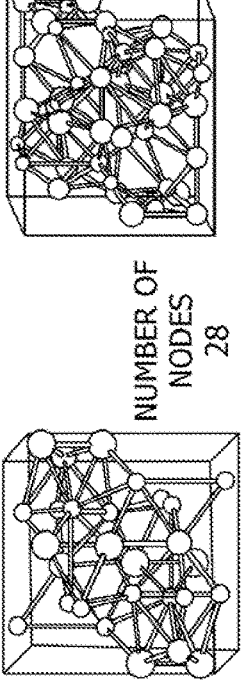
FIG. 32 is a view illustrating an example summarizing results of Example 1 and Comparative Example 1.
Figure 32:
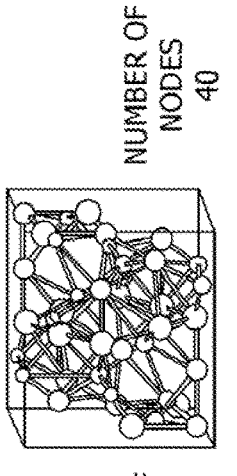
Figure 32:
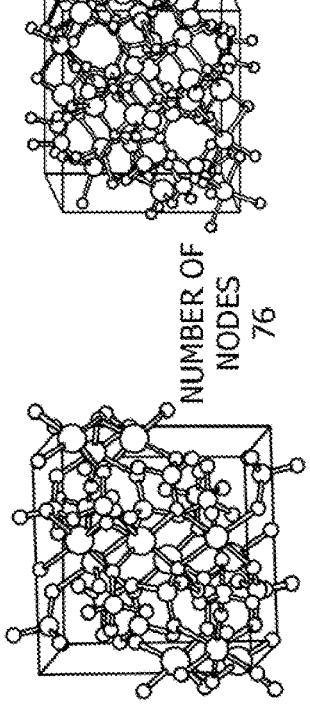
Figure 32:
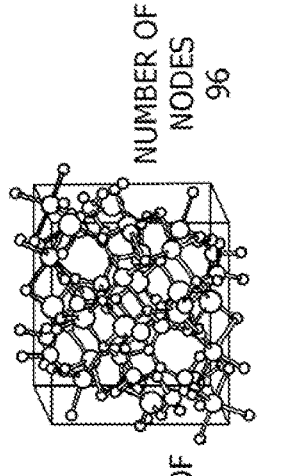

FIG. 32 illustrates a diagram summarizing results of Example 1 and Comparative Example 1.

In Example 1, in the number of nodes of the conflict graph (the number of bits required for calculation), lithium nodes are "8×16=128", manganese nodes are "4×8=32", and phosphorus nodes are "16×16=256". Therefore, in Example 1, the number of nodes in the conflict graph is "128+32+256=416".

Whereas, when the degree of similarity was calculated without deleting nodes of oxygen atoms contained the unit cell of the ionic crystal A and the ionic crystal B, (Comparative Example 1; a comparative example for Example 1), the number of nodes required for the calculation of the degree of similarity was "3104" as described above, which was much larger than that of Example 1.

Moreover, in Example 1, for the ionic crystal A and the ionic crystal B, the number of atoms to be a common substructure was "18", and the degree of similarity based on the above Equation (2) was computed as "0.546".

Whereas, in the comparative example (Comparative Example 1) for Example 1, the number of atoms to be a common substructure was "55", and the degree of similarity based on the above Equation (2) was computed to be "0.648".

From these results, it was possible to confirm that a difference in the degree of similarity between Example 1 and Comparative Example 1 was about 0.1, which was a relatively close value.

Example 2

In Example 2, the degree of similarity between the ionic crystal A and the ionic crystal B was computed similarly to Example 1 except that S129 and S130 in FIG. 26 were performed, and a graph was multiplied by an integer and then the degree of similarity was computed.

Specifically, for example, regarding the ionic crystal A and the ionic crystal B in which all nodes of oxygen atoms are deleted, the degree of similarity was calculated by doubling the unit cell of the ionic crystal A to make the number of nodes "80" and tripling the unit cell of the ionic crystal B to make the number of nodes "84", in order to reduce a difference between the numbers of nodes contained in the unit cells of the individual crystals.

FIG. 33 illustrates a diagram summarizing a result of Example 2.

In Example 2, for the ionic crystal A and the ionic crystal B, the number of bits required for calculation was "2496", the number of atoms to be a common substructure was "43", and the degree of similarity based on the above Equation (2) was computed as "0.525".

Since this degree of similarity has been computed by making the numbers of nodes in the unit cells in the individual crystals uniform, it can be considered that the accuracy is higher than the degree of similarity in Example 1.

Furthermore, in Example 2, as described above, the number of bits required for calculation was "2496", and it was possible to compute the degree of similarity with a smaller number of bits than that in Comparative Example 1 in which the oxygen atoms were not deleted, after the numbers of nodes in the unit cells in individual crystals are made uniform.

Example 3

In Example 3, the degree of similarity was computed similarly to Example 1 except that the ionic crystals targeted for computation of the degree of similarity were crystals (six types) whose composition formula is represented by "$Li_2MP_2O_7$" (M=Fe, Co, Mn, Ba), and nodes of oxygen atoms were deleted.

Furthermore, as a comparative example (Comparative Example 2) corresponding to Example 3, the degree of similarity was computed without deleting nodes of oxygen atoms.

FIG. 34 illustrates a relationship between a type of an ionic crystal and a computed degree of similarity in Example 3 and Comparative Example 2.

Here, among the six types of ionic crystals illustrated in FIG. 34, crystals of "M=Ba" (ICSD #107724 and ICSD #41433) are crystals having a different structural type from other crystals.

As illustrated in FIG. 34, in Example 3, the degree of similarity between crystals in which M is any of Fe, Co, or Mn is high, and the degree of similarity between crystals in which M is Ba is also high. Whereas, the degree of similarity between crystals in which M is any of Fe, Co, or Mn and crystals in which M is Ba is low, and it can be seen that correct classification has been made in accordance with types of crystalline structures.

Furthermore, FIG. 35 illustrates a relationship between a type of an ionic crystal and the number of bits required for calculating a degree of similarity in Example 3 and Comparative Example 2.

As illustrated in FIG. 35, the number of bits required for computing the degree of similarity was 656 or more and 832 or less in Example 3, and 3792 or more and 3968 or less in Comparative Example 2. From this, it was possible to confirm that, in Example 3, the number of bits required for the calculation can be reduced, and a highly accurate degree of similarity that can be correctly classified in accordance with the type of crystalline structure can be computed.

Example 4

In Example 4, the degree of similarity was computed similarly to Example 3 except that the ionic crystals targeted for computation of the degree of similarity were crystals represented by individual composition formulas of CsCl, KCl, NaCl, NaF, LiF, and LiCl, and a halogen atom (Cl or F), which is an example of the anionic atom, was deleted.

Note that, in the ionic crystals targeted in Example 4, CsCl is ICSD #257256, KCl is ICSD #28938, NaCl is ICSD #28048, NaF is ICSD #29128, LiF is ICSD #44879, and LiCl is ICSD #52235.

Furthermore, in Example 4, for CsCl (ICSD #257256), two cells in each direction of an a-axis, a b-axis, and a c-axis were targeted for expressing as a graph, and, for other crystals, two cells in each direction of the a-axis and the b-axis and one cell in the direction of the c-axis were targeted for expressing as a graph. The number of nodes in each graph was eight.

FIG. 36 illustrates a relationship between a type of an ionic crystal and a computed degree of similarity in Example 4.

Here, in the six types of ionic crystals illustrated in FIG. 36, CsCl (ICSD #257256) is a simple cubic cell, and other crystals are face-centered cubic cells.

As illustrated in FIG. 36, in Example 4, while the degree of similarity between crystals that are face-centered cubic cells is high, the degree of similarity between a crystal of the simple cubic cell and a crystal of the face-centered cubic cell is low, which shows that correct classification has been made in accordance with the types of crystalline structures.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A crystal analysis method for a computer to execute a process comprising:
    creating a graph that indicates data of repeating unit cell in an ionic crystal and data of an adjacent repeating unit cell that is adjacent to the repeating unit cell;
    analyzing the ionic crystal based on the graph; and
    when a number of first intra-cell nodes that indicate data of an anionic atom bonded to a cationic atom in the repeating unit cell is n, setting a number of second intra-cell nodes that indicate data of the anionic atom in the repeating unit cell to 0, wherein:
    the data of the repeating unit cell includes a plurality of intra-cell nodes that indicate data of atoms in the repeating unit cell, the plurality of intra-cell nodes include the first intra-cell node and the second intra-cell node,
the creating includes:
  creating a first graph for a first crystal; and
  creating a second graph for a second crystal,
the analyzing includes calculating a degree of similarity between the first crystal and the second crystal based on the first graph and the second graph,
the calculating includes multiplying at least one of the repeating unit cell for the first graph or the repeating unit cell for the second graph by an integer so that numbers of the intra-cell node in the first graph and numbers of the intra-cell node in the second graph are approximated, and
characteristics of a crystal are predicted by using a learning model which is created by a machine learning in which learning is performed by using a training data set including the first graph and the second graph and characteristics of the first crystal and the second crystal as a label.

2. The crystal analysis method according to claim 1, wherein the process further comprises:
when cationic atoms in the repeating unit cell are chemically bonded to each other, determining that a bond order of a chemical bond between the cationic atoms is a number of chemical bonds between the cationic atoms via the anionic atom whose number is 0.

3. The crystal analysis method according to claim 1, wherein
the data of the repeating unit cell includes an intra-cell edge that indicates data of chemical bonds between two atoms in the repeating unit cell, and
the data of the adjacent repeating unit cell includes an extension node that indicates data of atoms in the adjacent repeating unit cell and an extension edge that indicates data of chemical bonds between an atom that corresponds to the intra-cell node in the repeating cell unit and an atom that corresponds to the extension node.

4. The crystal analysis method according to claim 1, wherein the graph includes a loop edge that indicates data of a virtual chemical bond between an atom X in the repeating cell unit and an atom Y in the repeating cell that corresponds to an atom Y' in the adjacent repeating unit cell that chemically bonds to the atom X.

5. The crystal analysis method according to claim 1, wherein the calculating includes searching for a maximum independent set of a conflict graph between the first graph and the second graph by using Equation 1 below:

[Equation 1]

$$E = -\alpha \sum_i x_i + \beta \sum_i \sum_j c'_{i,j} x_i x_j \ldots \text{式} \quad (1)$$

wherein, in the Equation 1,
the E is a Hamiltonian in which minimizing the E means searching for the maximum independent set,
the $c'_{ij}$ is a coefficient that represents a weight regarding a bond order between an i-th node and a j-th node in the conflict graph,
the $x_i$ is a binary variable that represents that the i-th node is 0 or 1,
the $x_j$ is a binary variable that represents that the j-th node is 0 or 1, and
the $\alpha$ and the $\beta$ are positive numbers.

6. The crystal analysis method according to claim 5, wherein the searching includes minimizing a Hamiltonian in the above Equation 1 by an annealing method.

7. The crystal analysis method according to claim 1, wherein the calculating includes searching for a maximum independent set by using Equation 2 below:

[Equation 2]

$$S(G_A, G_B) = \delta \max\left\{\frac{|V_C^A|}{|V_A|}, \frac{|V_C^B|}{|V_B|}\right\} + (1-\delta)\min\left\{\frac{|V_C^A|}{|V_A|}, \frac{|V_C^B|}{|V_B|}\right\} \ldots \text{式} \quad (2)$$

wherein, in the Equation 2,
the $S(G_A, G_B)$ which is a number from 0 to 1 represents a degree of similarity between the first crystal and the second crystal,
the $V_A$ represents a total number of atoms in the first crystal,
the $V_c^A$ represents a number of atoms in the first crystal included in the maximum independent set,
the $V_B$ represents a total number of atoms in the second crystal,
the $V_c^B$ represents a number of atoms in the second crystal included in the maximum independent set, and
the $\delta$ is a number from 0 to 1.

8. A crystal analysis device comprising:
one or more memories; and
one or more processors coupled to the one or more memories and the one or more processors configured to:
  create a graph that indicates data of repeating unit cell in an ionic crystal and data of an adjacent repeating unit cell that is adjacent to the repeating unit cell;
  analyze the ionic crystal based on the graph; and
  when a number of first intra-cell nodes that indicate data of an anionic atom bonded to a cationic atom in the repeating unit cell is n, set a number of second intra-cell nodes that indicate data of the anionic atom in the repeating unit cell to 0, wherein:
  the data of the repeating unit cell includes a plurality of intra-cell nodes that indicate data of atoms in the repeating unit cell,
  the plurality of intra-cell nodes include the first intra-cell node and the second intra-cell node,
  the one or more processors further are configured to:
    create a first graph for a first crystal;
    create a second graph for a second crystal;
    calculate a degree of similarity between the first crystal and the second crystal based on the first graph and the second graph, and
    multiply at least one of the repeating unit cell for the first graph or the repeating unit cell for the second graph by an integer so that numbers of the intra-cell node in the first graph and numbers of the intra-cell node in the second graph are approximated, and
  characteristics of a crystal are predicted by using a learning model which is created by a machine learning in which learning is performed by using a training data set including the first graph and the second graph and characteristics of the first crystal and the second crystal as a label.

9. The crystal analysis device according to claim 8, wherein the one or more processors are configured to, when cationic atoms in the repeating unit cell are chemically bonded to each other, determine that a bond order of a chemical bond between the cationic atoms is a number of chemical bonds between the cationic atoms via the anionic atom whose number is 0.

10. The crystal analysis device according to claim 8, wherein
the data of the repeating unit cell includes an intra-cell edge that indicates data of chemical bonds between two atoms in the repeating unit cell, and
the data of the adjacent repeating unit cell includes an extension node that indicates data of atoms in the adjacent repeating unit cell and an extension edge that indicates data of chemical bonds between an atom that corresponds to the intra-cell node in the repeating cell unit and an atom that corresponds to the extension node.

11. The crystal analysis device according to claim 8, wherein the graph includes a loop edge that indicates data of a virtual chemical bond between an atom X in the repeating cell unit and an atom Y in the repeating cell that corresponds to an atom Y' in the adjacent repeating unit cell that chemically bonds to the atom X.

12. The crystal analysis device according to claim 8, wherein the one or more processors further are configured to search for a maximum independent set of a conflict graph between the first graph and the second graph by using Equation 3 below:

[Equation 3]

$$E = -\alpha \sum_i x_i + \beta \sum_i \sum_j c'_{i,j} x_i x_j \quad \ldots \text{式} \quad (1)$$

wherein, in the Equation 3,
the E is a Hamiltonian in which minimizing the E means searching for the maximum independent set,
the $c'_{ij}$ is a coefficient that represents a weight regarding a bond order between an i-th node and a j-th node in the conflict graph,
the $x_i$ is a binary variable that represents that the i-th node is 0 or 1,
the $x_j$ is a binary variable that represents that the j-th node is 0 or 1, and
the $\alpha$ and the $\beta$ are positive numbers.

13. The crystal analysis device according to claim 12, wherein the one or more processors further are configured to minimize a Hamiltonian in the above Equation 3 by an annealing method.

14. The crystal analysis device according to claim 8, wherein the one or more processors further are configured to search for a maximum independent set by using Equation 4 below:

[Equation 4]

$$S(G_A, G_B) = \delta \max\left\{\frac{|V_C^A|}{|V_A|}, \frac{|V_C^B|}{|V_B|}\right\} + (1-\delta)\min\left\{\frac{|V_C^A|}{|V_A|}, \frac{|V_C^B|}{|V_B|}\right\} \quad \ldots \text{式} \quad (2)$$

wherein, in the Equation 4,
the $S(G_A, G_B)$ which is a number from 0 to 1 represents a degree of similarity between the first crystal and the second crystal,
the $V_A$ represents a total number of atoms in the first crystal,
the $V_c^A$ represents a number of atoms in the first crystal included in the maximum independent set,
the $V_B$ represents a total number of atoms in the second crystal,
the $V_c^B$ represents a number of atoms in the second crystal included in the maximum independent set, and
the $\delta$ is a number from 0 to 1.

\* \* \* \* \*